US011497439B2

(12) United States Patent
Anderson et al.

(10) Patent No.: US 11,497,439 B2
(45) Date of Patent: Nov. 15, 2022

(54) PATTERN RECOGNITION SYSTEM FOR CLASSIFYING THE FUNCTIONAL STATUS OF PATIENTS WITH CHRONIC HEART, LUNG, AND PULMONARY VASCULAR DISEASES

(71) Applicant: Shape Medical Systems, Inc., St. Paul, MN (US)

(72) Inventors: Stephen T. Anderson, North Oaks, MN (US); David M. Anderson, White Bear Lake, MN (US); Dean J. MacCarter, Englewood, CO (US)

(73) Assignee: Shape Medical Systems, Inc., Saint Paul, MN (US)

( * ) Notice: Subject to any disclaimer, the term of this patent is extended or adjusted under 35 U.S.C. 154(b) by 224 days.

(21) Appl. No.: 16/583,034

(22) Filed: Sep. 25, 2019

(65) Prior Publication Data

US 2020/0281524 A1 Sep. 10, 2020

Related U.S. Application Data

(60) Provisional application No. 62/814,215, filed on Mar. 5, 2019.

(51) Int. Cl.
*A61B 5/091* (2006.01)
*A61B 5/00* (2006.01)
*A61B 5/083* (2006.01)

(52) U.S. Cl.
CPC .......... *A61B 5/4848* (2013.01); *A61B 5/0836* (2013.01); *A61B 5/091* (2013.01); *A61B 5/4884* (2013.01); *A61B 5/742* (2013.01)

(58) Field of Classification Search
CPC ..... A61B 5/4848; A61B 5/0836; A61B 5/091; A61B 5/4884; A61B 5/742
See application file for complete search history.

(56) References Cited

U.S. PATENT DOCUMENTS 4,463,764 A 8/1984 Anderson et al.
4,930,519 A 6/1990 Anderson et al.
(Continued)

FOREIGN PATENT DOCUMENTS

CN 101524274 A 9/2009
CN 103153184 A 6/2013
(Continued)

OTHER PUBLICATIONS

Fortuna, Armando de O., and John R. Gurd. "Numerically based design of an orifice plate flowmetering system for human respiratory flow monitoring." Annals of biomedical engineering 27.3: 356-365. (Year: 1999).*

(Continued)

*Primary Examiner* — Patrick Fernandes
*Assistant Examiner* — Liam A Wallace
(74) *Attorney, Agent, or Firm* — Merchant & Gould P.C.

(57) ABSTRACT

Systems and methods for evaluating patients are provided. An example includes receiving first cardiopulmonary exercise test data for the patient and plotting a first vector based on the first cardiopulmonary exercise test data, the first vector including a first point based on a rest value and a second point based on an exercise value. A first coordinate value of the first point and a first coordinate value of the second point may be based on mixed expired $CO_2$ ($PECO_2$) and a second coordinate value of the first point and a second coordinate value of the second point may be based on end tidal $CO_2$ ($PetCO_2$). The example may also include plotting a midpoint of the first vector and triggering display of the plotted vector and plotted midpoint. The plotted vector and plotted midpoint may be displayed over a coordinate grid having multiple physiological condition zones.

17 Claims, 16 Drawing Sheets

(56) References Cited

U.S. PATENT DOCUMENTS

| | | | |
|---|---|---|---|
| 5,398,695 | A | 3/1995 | Anderson et al. |
| 5,502,660 | A | 3/1996 | Anderson et al. |
| 5,925,831 | A | 7/1999 | Storsved |
| 6,089,105 | A | 7/2000 | Ricciardelli |
| 6,358,215 | B1 | 3/2002 | Ricciardelli |
| 6,659,962 | B2 | 12/2003 | Ricciardelli |
| 7,225,022 | B2 | 5/2007 | Anderson et al. |
| 7,713,211 | B2 | 5/2010 | Anderson et al. |
| 7,878,980 | B2 | 2/2011 | Ricciardelli |
| 8,342,178 | B2 | 1/2013 | Hengstenberg et al. |
| 8,459,261 | B2 | 6/2013 | Ricciardelli et al. |
| 8,460,203 | B2 | 6/2013 | Ricciardelli |
| 8,630,811 | B2 | 1/2014 | Anderson et al. |
| 8,768,463 | B2 | 7/2014 | Anderson et al. |
| 8,775,093 | B2 | 7/2014 | Anderson et al. |
| 10,010,264 | B2 | 7/2018 | Anderson et al. |
| 2002/0185131 | A1 | 12/2002 | Madaus et al. |
| 2003/0208106 | A1 | 11/2003 | Anderson et al. |
| 2004/0017475 | A1 | 1/2004 | Akers et al. |
| 2004/0138716 | A1 | 7/2004 | Kon et al. |
| 2004/0186389 | A1 | 9/2004 | Mau et al. |
| 2004/0260185 | A1 | 12/2004 | Anderson et al. |
| 2005/0115561 | A1 | 6/2005 | Stahmann et al. |
| 2009/0076347 | A1 | 3/2009 | Anderson et al. |
| 2009/0281415 | A1 | 11/2009 | Cupps et al. |
| 2009/0281443 | A1 | 11/2009 | Hengstenberg et al. |
| 2011/0208082 | A1 | 8/2011 | Madaus et al. |
| 2012/0130265 | A1 | 5/2012 | Cha et al. |
| 2012/0265447 | A1* | 10/2012 | Anderson ............ A61B 5/0205 702/19 |
| 2013/0324873 | A1 | 12/2013 | Babaeizadeh et al. |
| 2013/0345572 | A1 | 12/2013 | Karbing et al. |
| 2014/0163397 | A1* | 6/2014 | Anderson ............ A61B 5/0833 600/484 |

FOREIGN PATENT DOCUMENTS

| | | | | |
|---|---|---|---|---|
| EP | 2898823 | A1 * | 7/2015 | ........... A61B 5/0836 |
| KR | 20160027282 | A * | 3/2016 | ............. A61B 5/168 |

OTHER PUBLICATIONS

Arena et al., "The partial pressure of resting end-tidal carbon dioxide predicts major cardiac events in patients with systolic heart failure," Am Heart J, vol. 156, 2008, pp. 982-988.

Arena et al.: "Ventilatory Expired Gas at Low-Intensity Exercise Predicts Adverse Events and Is Related to Neurohormonal Markers in Patients with Heart Failure," J Card Fail, Aug. 2009; 15(6):482-8. Epub Feb. 10, 2009.

Arena et al: "Development of a Ventilatory Classification System in Patients with Heart Failure," Circulation, vol. 115, 2007, pp. 2410-2417.

Arena et al: "Influence of Heart Failure Etiology on the Prognostic Value of Peak Oxygen Consumption and Minute Ventilation/Carbon Dioxide Production Slope," Chest, vol. 128, 2005, pp. 2812-2817.

Arena et al: "The Minute Ventilation/Carbon Dioxide Production Slope is Prognostically Superior to the Oxygen Uptake Efficiency Slope," Journal of Cardiac Failure, vol. 13, No. 6, 2007, pp. 462-469.

Beaver et al.: "On-line computer analysis and breath-by-breath graphical display of exercise function tests," Journal of Applied Physiology, vol. 34, No. 1, Jan. 1973.

Davies et al.: "Enhanced Prognostic Value From Cardiopulmonary Exercise Testing in Chronic Heart Failure by Non-Linear Analysis: Oxygen Uptake Efficiency Slope," European Heart Journal, vol. 27, 2006, pp. 684-690.

Froelicher et al., "Exercise and the Heart," Mosby-Year Book, Inc. 1993, p. 38.

Gaine et al.: "Primary Pulmonary Hypertension," Lancet, vol. 352, 1998, pp. 719-725.

Guazzi et al.: "Ventilatory Efficiency and Dyspnea on Exertion Improvements are Related to Reduced Pulmonary Pressure in Heart Failure Patients Receiving Sildenafil," Int J Cardiol., Mar. 27, 2009, [Epub ahead of print] PMID: 19329196.

Hansen et al.: "Mixed-Expired and End-Tidal CO2 Distinguish Between Ventilation and Perfusion defects During Exercise testing in Patients with Lung and Heart Diseases," Chest, vol. 132, Jun. 15, 2007, pp. 977-983.

Hollenberg et al: "Oxygen Uptake Efficiency Slope: An Index of Exercise Performance and Cardiopulmonary Reserve Requiring Only Submaximal Exercise," Journal of American College of Cardiology, vol. 36, No. 1, 2000, pp. 194-201.

International Search Report and the Written Opinion from International Application No. PCT/US2010/050197, dated Dec. 27, 2010.

International Search Report and Written Opinion for Application No. PCT/US2015/020703 dated Jul. 13, 2015.

Kim et al., "A Multivariable Index (MVI) for Grading Exercise Gas Exchange Severity in Patients with Pulmonary Arterial Hypertension and Heart Failure," Pulmonary Medicine, vol. 2012, Article ID 962598, doi:10.1155/2012/962598 (2012).

Kleber et al.: "Impairment of Ventilatory Efficiency in Heart Failure: Prognostic Impact," Circulation, vol. 101, 2000, pp. 2803-2809.

Marieb, "Human Anatomy and Physiology," Benjamin/Cummings Publishing Company, 1992, p. 749.

McRae III et al.: "The Oxygen Uptake Efficiency Slope as a Predictor of Mortality in Chronic Heart Failure," Journal of American College Cardiology, vol. 43, 2002, abstract 856-3, p. 183A.

Miyamoto et al.: "Clinical Correlates and Prognostic Significance of Six-minute Walk Test in Patients with Preimary Pulmonary Hypertension," American Journal of Respiratory and Critical Care Medicine, vol. 161, 2000, pp. 487-492.

Ponikowski et al: "Enhanced Ventilatory Response to Exercise in Patients With Chronic Heart Failure and Preserved Exercise Tolerance: Marker of Abnormal Cardiorespiratory Reflex Control and Predictor of Poor Prognosis".

Robbins et al: "Ventilatory and Heart Rate Response to Exercise: Better Predictors of Heart Failure Mortality Than Peak Oxygen Consumption," Circulation, vol. 100, 1999, pp. 2411-2417.

Vivekananthan et al.: "Heart Rate Recovery After Exercise is a Predictor of Mortality, Independent of the Angiographic Severity of Coronary Disease," Journal of the American College of Cardiology, vol. 42, No. 5, 2003, pp. 831-838.

Watanabe et al: "Heart Rate Recovery Immediately After Treadmill Exercise and Left Ventricular Systolic Dysfunction as Predictors of Mortality: The Case of stress Echocardiography," Circulation, vol. 104, 2001, pp. 1911-1916.

Wensel et al.: "Assessment of Survival in Patients With Primary Pulmonary Hypertension," Circulation, vol. 106, 2002, pp. 319-324.

Woods et al.: "A Pulmonary Hypertension Gas Exchange Severity (PH-GXS) Score to Assist With the Assessment and Monitoring of Pulmonary Arterial Hypertension," American Journal of Cardiology, vol. 109, Apr. 1, 2012, pp. 1066-1072.

Woods et al.: "The usefulness of submaximal exercise gas exchange to define pulmonary arterial hypertension," Journal of Heart and Lung Transplantation, vol. 30, Oct. 1, 2011, pp. 1133-1142.

Yasunobu et al., "End-tidal PCO2 Abnormality and Exercise Limitation in Patients with Primary Pulmonary Hypertension," Chest, vol. 127, 2005; pp. 1637-1646.

* cited by examiner

| Key | Test Key | Phase | Breath Count | PeCO2 | PetCO2 | VCO2 | VO2 | VT | Heart Rate | RR | Bar. Press. | ... |
|---|---|---|---|---|---|---|---|---|---|---|---|---|
| 386 | 327 | Rest | data | data | data | data | data | data | data | data | data | data |
| 387 | 327 | Exercise | data | data | data | data | data | data | data | data | data | data |
| 388 | 327 | Recovery | data | data | data | data | data | data | data | data | data | data |

Figure 3

```
IF VQ graph normal then
    Impression = "The V/Q graph supports normal pulmonary ventilation to perfusion."
If VQ graph shows Lung Dysfunction
    Impression = "The V/Q graph supports mismatching indicative of lung dysfunction
                (COPD/RLD) with limited increase in ventilation relative to perfusion."
IF VQ Graph shows PAH
    If Vector from rest to peak points left
        Impression = "The V/Q graph provides supportive evidence of pulmonary arterial
                    hypertension with V/Q mismatching (Note leftward direction of from
                    rest to end exercise and reduced resting PETCO2)."
    ELSE
        Impression = "The V/Q graph shows reduced lung ventilation and perfusion,
                    supportive of the likelihood of LV dysfunction and secondary PH"

IF VQ graph shows Transitional
     Impression = "It is possible that this patient has risk factors for left heart
                 disease and/or for pre-capillary PH"
     IF ( Resting PetCO2 >= PETCO2 Quadrant Divider ) And
        ( Peak PECO2 <= PECO2 Quadrant Divider Then add this text
        Impression = Impression + " with support for secondary PH as a comorbidity."

If (Peak PetCO2 < Resting PetCO2) And
        (Peak PECO2 > Resting PECO2) Then add this text
       Impression = Impression + " Decreasing PetCO2 and increasing PECO2 during
                            exercise indicated possible left ventricular dysfunction."
     Else If ( Peak PetCO2 > Resting PetCO2) And
             ( Peak PECO2 <  Resting PECO2) Then add this text
        Impression = Impression + " Increasing PetCO2 and decreasing PeCO2 indicates
                                    possible exercise induced bronchospasm."

If this patient has multiple tests to review add this text.  Retest Angle is the vector
from the first test to the latest test.

Impression = Impression + " The latest retest shows "
    IF Retest Vector Index = 1 Then add this text
        Impression = Impression + "both lung ventilation and perfusion improved
                                during exercise."
    IF Retest Vector Index = 2 Then add this text
        Impression = Impression +  "there was an improvement in lung ventilation but not
                                perfusion during exercise."
    IF Retest Vector Index = 4 Then add this text
        Impression = Impression + "there was an improvement in perfusion but not lung
                                ventilation during exercise."
    IF Retest Vector Index = 3 then add this text
        Impression = Impression + "there was no improvement in perfusion or lung
                                ventilation during exercise."
```

Figure 9

PATTERN RECOGNITION SYSTEM FOR CLASSIFYING THE FUNCTIONAL STATUS OF PATIENTS WITH CHRONIC HEART, LUNG, AND PULMONARY VASCULAR DISEASES

RELATED APPLICATIONS

This application is related to and claims priority to U.S. Provisional Patent Application No. 62/814,215, titled "A PATTERN RECOGNITION SYSTEM FOR CLASSIFYING THE FUNCTIONAL STATUS OF PATIENTS WITH CHRONIC HEART, LUNGS, AND PULMONARY VASCULAR DISEASES" and dated Mar. 5, 2019, which is hereby incorporated by reference in its entirety.

This application is also related to U.S. Pat. No. 8,630,811, titled "Method for combining individual risk variables derived from cardiopulmonary exercise testing into a single variable" and dated Jan. 14, 2014; U.S. Pat. No. 8,775,093, titled "Pattern Recognition System for Classifying the Functional Status of Patients with Pulmonary Hypertension, Including Pulmonary Arterial and Pulmonary Vascular Hypertension" and dated Jul. 8, 2014; and U.S. Pat. No. 10,010,264, titled "Pattern recognition system for quantifying the likelihood of the contribution of multiple possible forms of chronic disease to patient reported dyspnea" and dated Jul. 3, 2018; each of which are hereby incorporated by reference in their entireties.

BACKGROUND

The present disclosure relates generally to the field of medical evaluation, assessment, and/or diagnosis of the patient complaint of dyspnea (also called shortness of breath) with or without fatigue and specifically, to a process of identifying patients with heart failure, left ventricular dysfunction, chronic obstructive and restrictive lung disease (COPD), pulmonary arterial hypertension (PAH) and secondary pulmonary hypertension (PH) and classifying the functional status of these patients to assess the severity of the disease. The present method provides a more sensitive, physiologic, and easier to use method than currently available classification systems. In addition, the present disclosure provides feedback during long-term follow-up and treatment of patients with chronic diseases.

The early symptoms of chronic disease—such as dyspnea, dizziness and fatigue—are often mild and are common to many other conditions, including deconditioning. At rest, there are often no symptoms and no apparent signs of illness. As a result, diagnosis can be delayed for months or even years meaning that the underlying disease is frequently not recognized until the disease is relatively advanced, thus more difficult to treat.

Pulmonary Hypertension (PH) is hemodynamically classified as pre-capillary (as seen in idiopathic pulmonary hypertension (IPAH)) or post-capillary (as seen in heart failure with either reduced ejection fraction (HFrEF) or heart failure with preserved ejection fraction (HFpEF)). Overlaps in these conditions exist. Some patients present with risk factors for left heart disease but pre-capillary PH, whereas patients with HFpEF may have combined pre- and post-capillary PH. Patients with atypical IPAH share features of both typical IPAH and PH-HFpEF suggesting that there may be a continuum between these conditions.

The non-specific nature of symptoms associated with PH means that the diagnosis cannot be made on symptoms alone. Neither can it be diagnosed using a 6 minute walk test. A series of investigations is required to make an initial diagnosis, to refine that diagnosis in terms of clinical class of a disease, and to evaluate the degree of functional and hemodynamic impairment. Current PH evaluation and classification (type, functional capacity, hemodynamics) methods include blood tests and immunology, HIV test, thoracic/abdominal ultrasound scan, 6-minute walk test (6-MWT), peak $VO_2$, right heart catheterization, and vaso-reactivity testing. It is with exercise that the sympathetic and neuro-hormonal systems trigger increased vasoconstriction of the pulmonary arteriolar vascular beds, thus causing an elevation in pulmonary vascular resistance and reduced blood flow through the pulmonary vascular circuit and reduced gas exchange at the capillary/alveolar junction. The reduced blood flow is mismatched to the air flow in the bronchioles and alveoli—also known as Ventilation/Perfusion (V/Q) mismatching.

It is often that the exercise state is not evaluated by any pulmonary function parameters that truly represent both lung ventilation and also perfusion (cardiac output) as related to actual gas exchange in the lungs. Adequate gas exchange during exercise is dependent upon and blood flow and breathing reserve. Instead, walking distance and may be peak oxygen uptake are measured which are "secondary outcomes" of gas exchange.

The major shortcoming of the existing classification systems for Heart Failure and Pulmonary Hypertension (NYHA and WHO) systems is that they rely on subjective observations by the patient and interpretation of those observations by the physician.

The 6-minute walk test, while simple and convenient, has many limitations including issues relating to reproducibility, sensitivity, and essentially a work plateau in functional assessment when patients have less functional impairment.

The logistics of performing an exercise test to maximal exertion, including laboratory staffing, direct physician supervision and test duration, in addition to the increased level of patient discomfort, does not lend to conducting this procedure in a serial fashion over short time intervals (i.e., several weeks-months). In addition, it has been found that maximum exercise levels are not representative of lower level, activities of daily living.

SUMMARY

The present advance, to a large extent, obviates the problems discussed in the foregoing for the NYHA/WHO Classification system, for peak $VO_2$ testing for functional classification, and for the 6-minute hall walk for therapy tracking. In accordance with the present disclosure, a new method has been found for a pattern recognition system that explains gas exchange in the lungs during exercise consisting of 1) a cardiopulmonary exercise gas exchange analyzer that gathers the observations to be classified or described, 2) a feature extraction mechanism that computes numeric information from the observations, and 3) a classification or description scheme that does the actual job of classifying or describing observations based on the extracted features.

BRIEF DESCRIPTION OF THE DRAWINGS

FIG. 3 illustrates an organization of the measured data once it is acquired from the cardiopulmonary exercise gas exchange analyzer.

FIG. 9 illustrates example logic used to provide the Impressions Statement for explanation of the test results.

DETAILED DESCRIPTION

Figure 1:
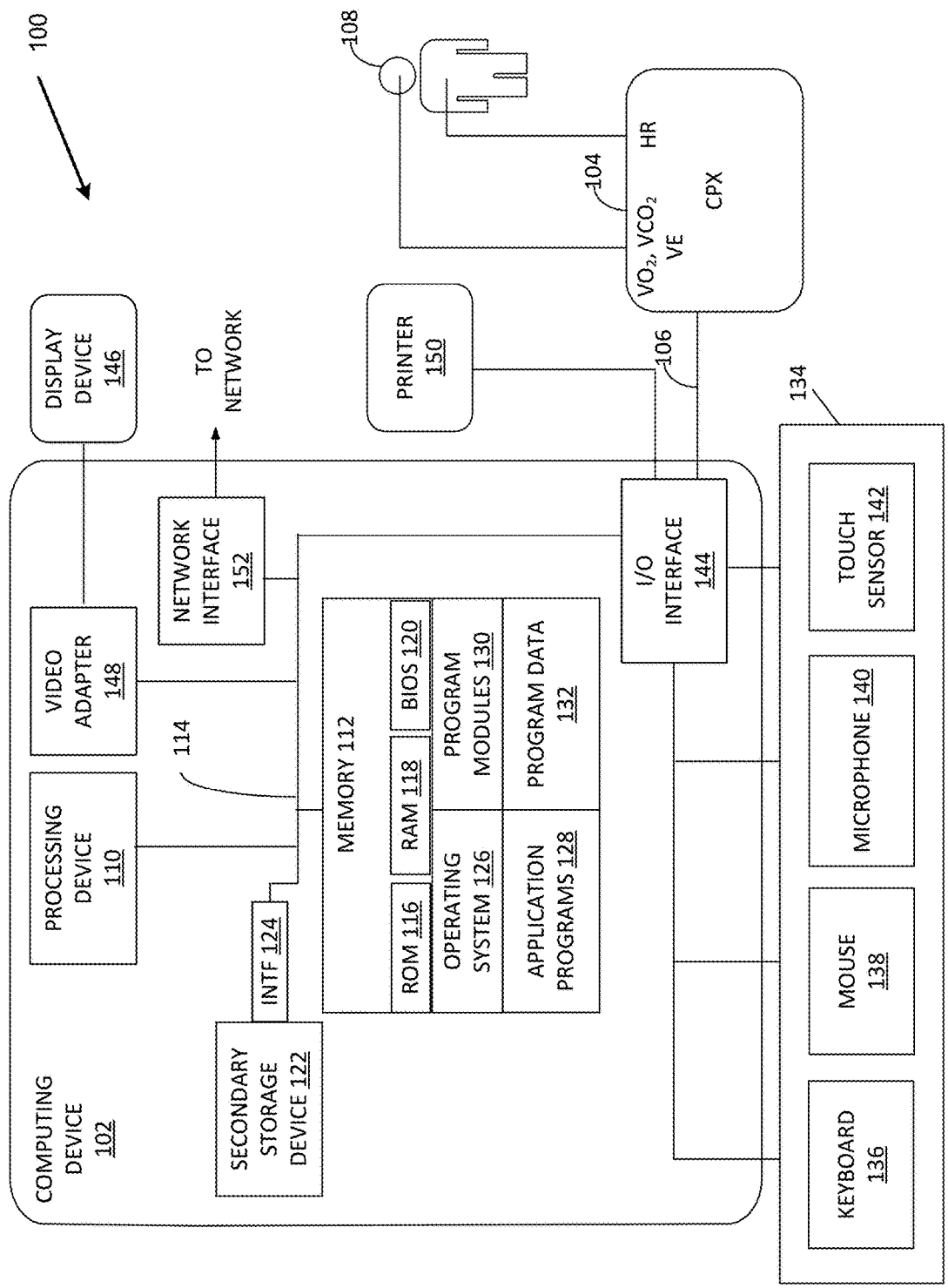
FIG. 1 is a schematic drawing that illustrates the functional components of a cardiopulmonary exercise (CPX) testing system usable with the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following detailed description, including the use of patient data, is intended to be exemplary of a preferred method of utilizing the concepts of the present disclosure and is not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

Example Advantages

Figure 4:
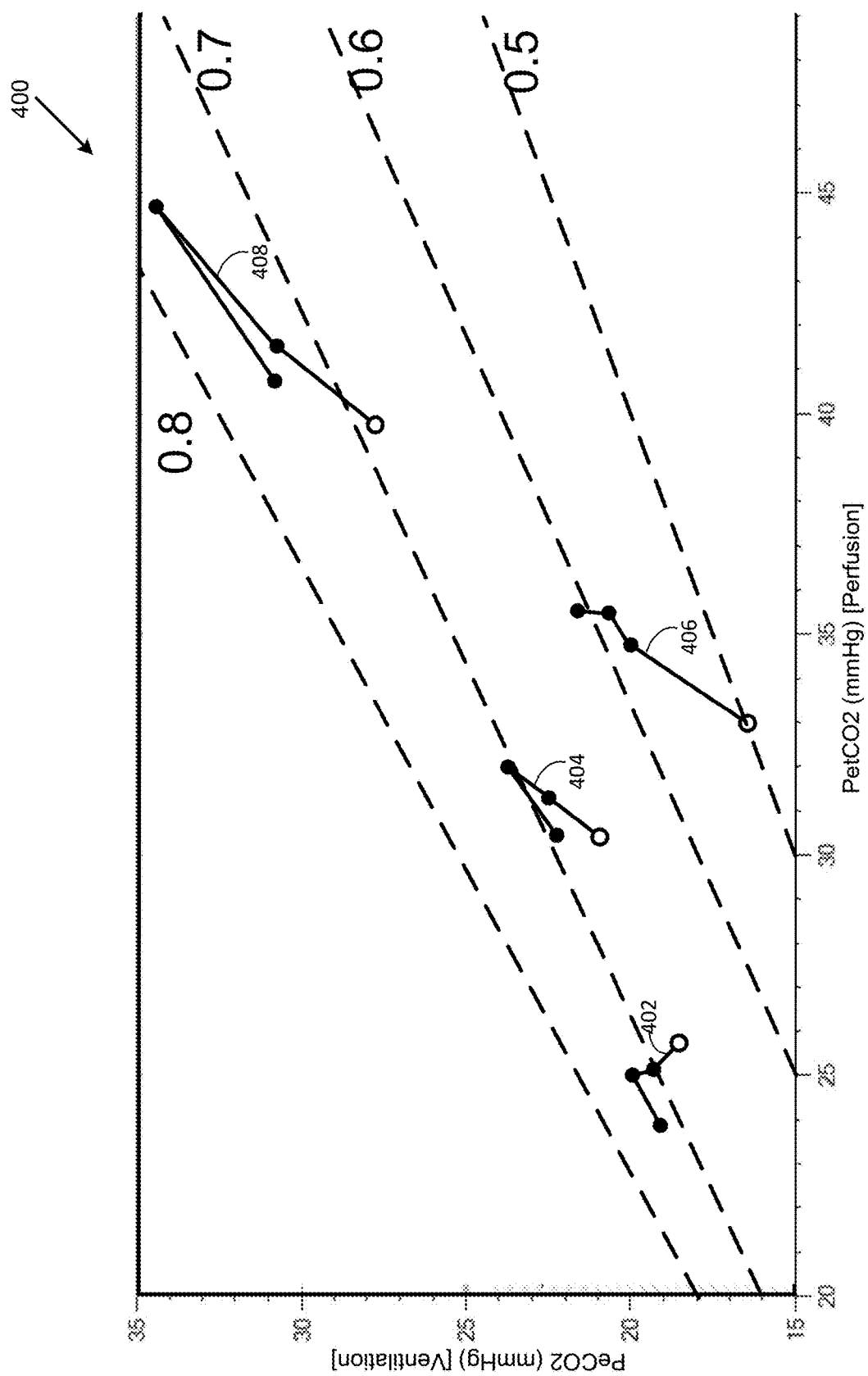
FIG. 4 illustrates an example plot showing the $PECO_2$/$PetCO_2$ ratio isopleths and the $PECO_2$ vs $PetCO_2$ axes and the separation between four disease classes.

FIG. 4 provides an example plot 400 of test values for $PECO_2$ (ventilation) and $PetCO_2$ (perfusion) at rest, during unloaded cycling, at anaerobic threshold, and at end of exercise for various physiologic states or disease types. In the example plot 400, $PECO_2$ ("y" axis) is plotted against $PetCO_2$ ("x" axis) for test datapoints with isopleths representing the ratios 0.5, 0.6, 0.7, and 0.8 shown. In this example, a test plot 402 represents example data from a test indicative of a subject with PAH, a test plot 404 represents example data from a test indicative of a subject with LVF, a test plot 406 represents example data from a test indicative of a subject with COPD, and a test plot 408 represents example data from a test indicative of a subject with a normal physiological state. Each of the test plots 402, 404, 406, and 408 include four connected data points. The first data point (shown as an open circle) corresponds to $PECO_2$ and $PetCO_2$ values at rest. The remaining data points correspond (in order) to $PECO_2$ and $PetCO_2$ values during unloaded cycling, at anaerobic threshold, and at end of exercise.

The use of plots similar to plot 400 to identify disease types for patients is discussed further in Hansen, James E., et al. "Mixed-expired and end-tidal CO2 distinguish between ventilation and perfusion defects during exercise testing in patients with lung and heart diseases." Chest 132.3 (2007): 977-983. However, no method for a computerized analysis of the resulting plot is presented or suggested. Also, the use of 4 data points per test may be confusing and unacceptable for clinical use. Beneficially, at least some implementations described herein only require 2 data points—the $PECO_2$ and $PetCO_2$ at rest and at peak or at the end of exercise. The resulting vector is further clarified as to length, direction and mean value of the coordinate points.

Furthermore, how such data can be used to track therapy is not addressed.

Using the method described below in accordance with the disclosure, the plot as in FIG. 6 uses a format similar to that shown in plot 400 (of FIG. 4) but with clearly defined "zones" that are used to identify the primary suspected disease causing the patient's shortness of breath. Using the measured values collected during a CPX test a single directional vector annotated with the median of the vector point identifies the zone, or disease classification. Thus, the physician's test interpretation is vastly simplified.

General Considerations

The present disclosure includes a pattern recognition system consisting of a) a cardiopulmonary exercise gas exchange analyzer that gathers the observations to be classified or described, b) a feature extraction mechanism that computes numeric information from the observations, and c) a classification or description scheme that does the actual job of classifying or describing observations based on the extracted features.

Figure 2:
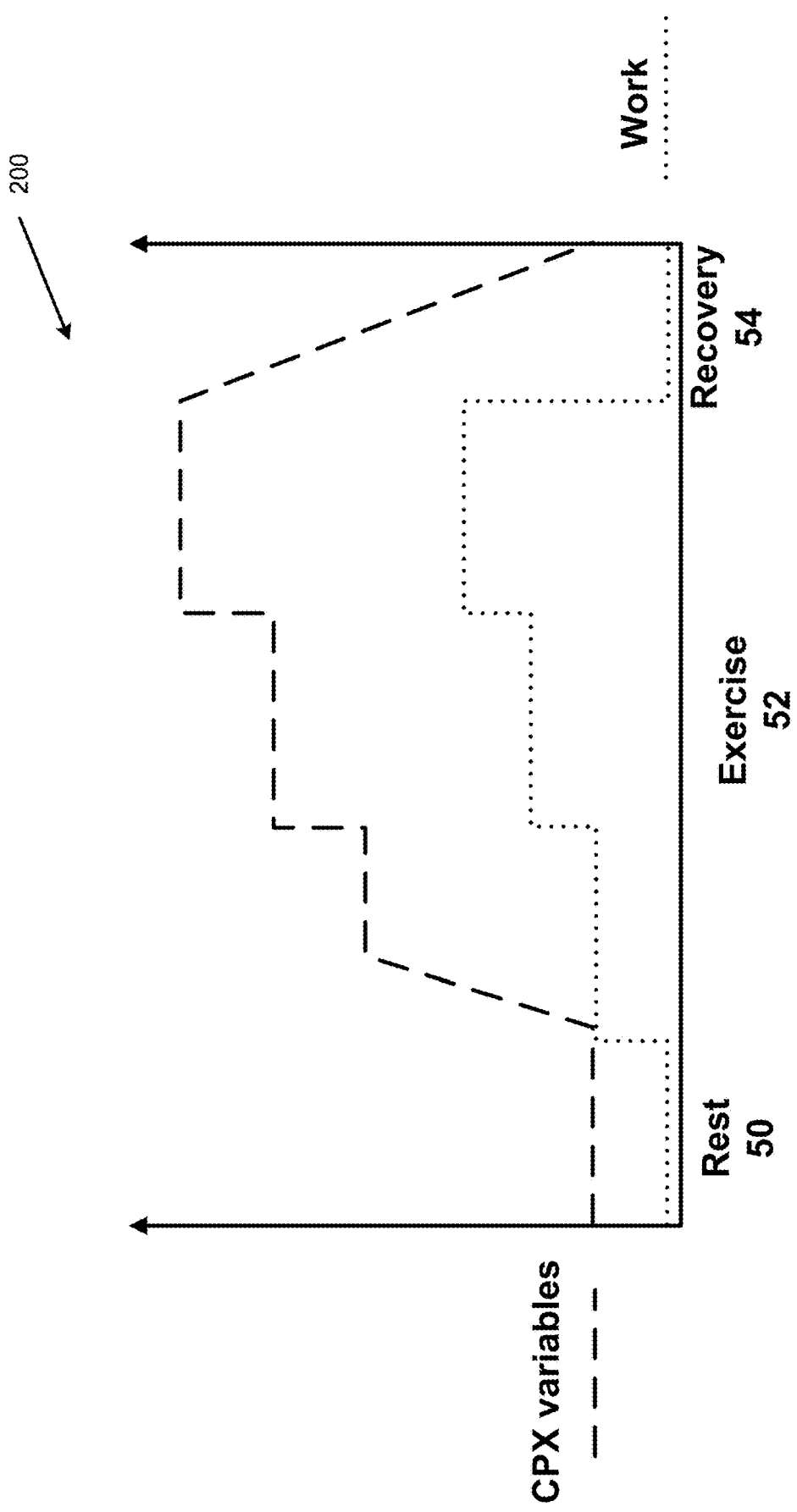
FIG. 2 is a schematic drawing that illustrates one form of exercise protocol that is used to place a volume load on the cardiopulmonary system.

Data Gathering:

As indicated and shown in graph 200 of FIG. 2, the general class of data utilized in the present disclosure, cardiopulmonary exercise gas exchange measurements, is obtained 1) at rest, 2) during physical exercise testing performed in accordance with a standardized incremental workload protocol as the forcing function to elicit physiologic changes resulting from the increasing workload, and 3) during a short recovery period following exercise termination. The data measured during exercise quantifies how an individual is able to function in the physical world in terms of the physiologic changes that the individual experiences when engaged in the performance of daily physical work.

The physiologic changes are measured using a CPX testing system to measure selected variables associated with one or more of oxygen consumption, $VO_2$, carbon dioxide production, $VCO_2$, end tidal $ETCO_2$, mixed expired $CO_2$, $PECO_2$, HR, and $SpO_2$.

As indicated, the data gathering aspect of the disclosure involves known techniques and analyses, and the calculations for formulating predictive assessments are readily available in the scientific literature (see the bibliography in References). However, by means of aspects of the feature extraction mechanism, classification and quantification scheme, the present disclosure enables an observer to gain new and valuable insight into the present condition and condition trends in patients. Thus, in accordance with a preferred method, a cardiopulmonary exercise gas exchange analysis is made for each test data set (FIG. 3). The performance of such a test is well understood by individuals skilled in the art, and no further explanation of this is believed necessary.

Equipment

With this in mind, an example system is shown in FIG. 1, which illustrates an example CPX testing system 100, whereby a CPX test may be conducted and the results displayed in accordance with the method of the present disclosure. In this example, the system includes a computing device 102. The computing device 102 illustrated in FIG. 1 can be used to execute the operating system, application programs, and software modules described herein.

The computing device 102 includes, in some embodiments, at least one processing device 110, such as a central processing unit (CPU). A variety of processing devices are available from a variety of manufacturers, for example, Intel or Advanced Micro Devices. In this example, the computing device 102 also includes a system memory 112, and a system bus 114 that couples various system components including the system memory 112 to the processing device 110. The system bus 114 is one of any number of types of bus structures including a memory bus, or memory controller; a peripheral bus; and a local bus using any of a variety of bus architectures.

Examples of computing devices suitable for the computing device 102 include a desktop computer, a laptop computer, a tablet computer, a mobile computing device (such as a smart phone, an iPod® or iPad® mobile digital device, or other mobile devices), or other devices configured to process digital instructions.

The system memory 112 includes read only memory 116 and random access memory 118. A basic input/output system 120 containing the basic routines that act to transfer information within computing device 102, such as during start up, is typically stored in the read only memory 116.

The computing device 102 also includes a secondary storage device 122 in some embodiments, such as a hard disk drive, for storing digital data. The secondary storage device 122 is connected to the system bus 114 by a secondary storage interface 124. The secondary storage devices 122 and their associated computer readable media provide nonvolatile storage of computer readable instructions (including application programs and program modules), data structures, and other data for the computing device 102.

Although the example environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory computer-readable media. Additionally, such computer readable storage media can include local storage or cloud-based storage.

A number of program modules can be stored in secondary storage device 122 or system memory 112, including an operating system 126, one or more application programs 128, other program modules 130 (such as the software engines described herein), and program data 132. The computing device 102 can utilize any suitable operating system, such as Microsoft Windows™, Google Chrome™ OS or Android, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 102 through one or more input devices 134. Examples of input devices 134 include a keyboard 136, mouse 138, microphone 140, and touch sensor 142 (such as a touchpad or touch sensitive display). Other embodiments include other input devices 134. The input devices are often connected to the processing device 110 through an input/output interface 144 that is coupled to the system bus 114. These input devices 134 can be connected by any number of input/output interfaces, such as a parallel port, serial port, game port, or a universal serial bus. Wireless communication between input devices and the interface 144 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 146, such as a monitor, liquid crystal display device, projector, or touch sensitive display device, is also connected to the system bus 114 via an interface, such as a video adapter 148. In addition to the display device 146, the computing device 102 can include various other peripheral devices, such as a printer 150 for printing reports or speakers (not shown).

When used in a local area networking environment or a wide area networking environment (such as the Internet), the computing device 102 is typically connected to the network through a network interface 152, such as an Ethernet interface or WiFi interface. Other possible embodiments use other communication devices. For example, some embodiments of the computing device 102 include a modem for communicating across the network.

The computing device 102 typically includes at least some form of computer readable media. Computer readable media includes any available media that can be accessed by the computing device 102. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 102.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device 102 illustrated in FIG. 1 is also an example of programmable electronics, which may include one or more such computing devices, and when multiple computing devices are included, such computing devices can be coupled together with a suitable data communication network so as to collectively perform the various functions, methods, or operations disclosed herein.

The equipment used in the exercise protocol can be a simple stair step of a known height or any other exercise modality such as a treadmill, bike, or hand ergometer. A CPX testing system 104 interfaces with the subject 108 (the subject is also referred to as a patient) during operation of the exercise test. The physiological variables may be selected from heart rate (HR), ventilation (VE), rate of oxygen uptake or consumption ($VO_2$) and carbon dioxide production ($VCO_2$), end tidal $CO_2$ ($PetCO_2$), mixed expired $CO_2$ ($PECO_2$), or other variables derived from these basic measurements. Physiological data collected is fed into the computing module 102 via a conductor 106, or other communication device.

In some implementations, the CPX system 104 includes a carbon dioxide sensor that can determine a concentration of carbon dioxide in a gas sample. Some implementations also include an oxygen sensor that can determine a concentration of oxygen in a gas sample. Some implementations do not include an oxygen sensor. The CPX system 104 may also include a flow volume sensor that can determine a flow volume of gas exhaled or inhaled by the patient. For example, the flow volume sensor may include one or more pressure transducers. The pressure transducers may determine a change in pressure as the gas passes through an orifice in tube through which the patient is breathing. Based on the change in pressure, the flow volume may be determined for the gas being exhaled and inhaled by the patient. These flow volume measurements may be combined with one or more of the $CO_2$ or $O_2$ measurements from the corresponding sensors to determine various parameters of the patient as described further herein.

The workload protocol is illustrated in FIG. 2 and is organized in to a rest phase 50, and exercise phase 52, and a recovery phase 54. Although not required, the workload may also be quantified, if a step is used as the exercise modality, by requiring the patient to maintain a desired stepping cadence by the addition of an audible metronome that guides the frequency of the steps taken during the exercise phase. Other prompts may be used to quantify or encourage patients to achieve or maintain a desired workload with other exercise modalities.

Data acquired by the CPX testing system may be stored in a relational database or another data store as illustrated in FIG. 3. Most importantly, data for each patient and each test is stored into separate subsets of data representing the rest phase 386, the exercise phase 387, and the recovery phase 388 for use by the feature extraction mechanism.

An advantage provided by at least some embodiments of the present disclosure is that many of the most prevalent chronic diseases can be identified without the measurement of oxygen consumption. The significance of this is that the most expensive and problematic sensor traditionally used in a CPX system can be excluded from the equipment shown in FIG. 1. Also, the most reliable O2 sensor is large, vibration-sensitive and bulky, while the differential pressure transducer (air flow) and $CO_2$ sensor are fingernail sized.

Some implementations include a gas analyzer that is an oxygen-sensorless analyzer. An oxygen-sensorless analyzer is a gas analyzer that does not include an oxygen sensor. For example, an oxygen-sensorless analyzer may include a differential pressure transducer and a carbon dioxide sensor but not an oxygen sensor.

An example embodiment includes a wearable equipment package that includes a differential pressure transducer and a $CO_2$ sensor and employs technology to communicate with a mobile computing device, such as a smart phone, rather than a personal computer such as a desktop personal computer (PC) or laptop PC. In some embodiments, the wearable equipment package includes an $O_2$ sensor. In some embodiments, the wearable package does not include an $O_2$ sensor. In some implementations, the mobile computing device may use an application (or app) that is installed and specially programmed to communicate with the wearable device over a wireless or wired protocol. The wearable equipment package could be used in a disease screening tool in primary care clinics. Whether a PC is used or a smart phone app is used, the outputs may be similar to those described further herein.

Feature Extraction Steps

Some implementation use the steps described below for feature extraction. Some implementations do not include all steps, perform the listed steps in an alternate order, or include different steps or variations of the steps listed below.

Step 1—Detection

Figure 6:
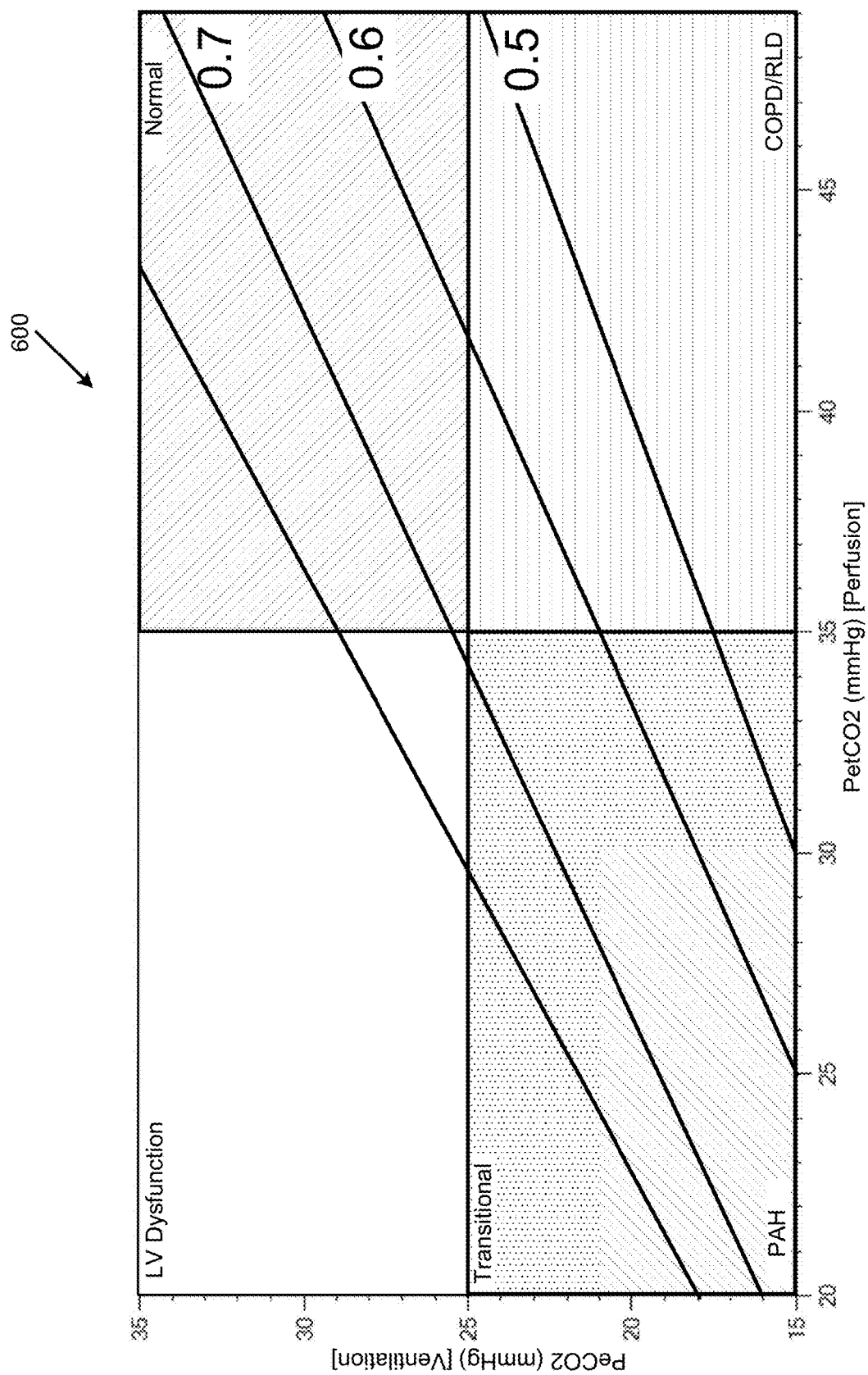
FIG. 6 illustrates an unpopulated test plot of the present disclosure.
Figure 7:
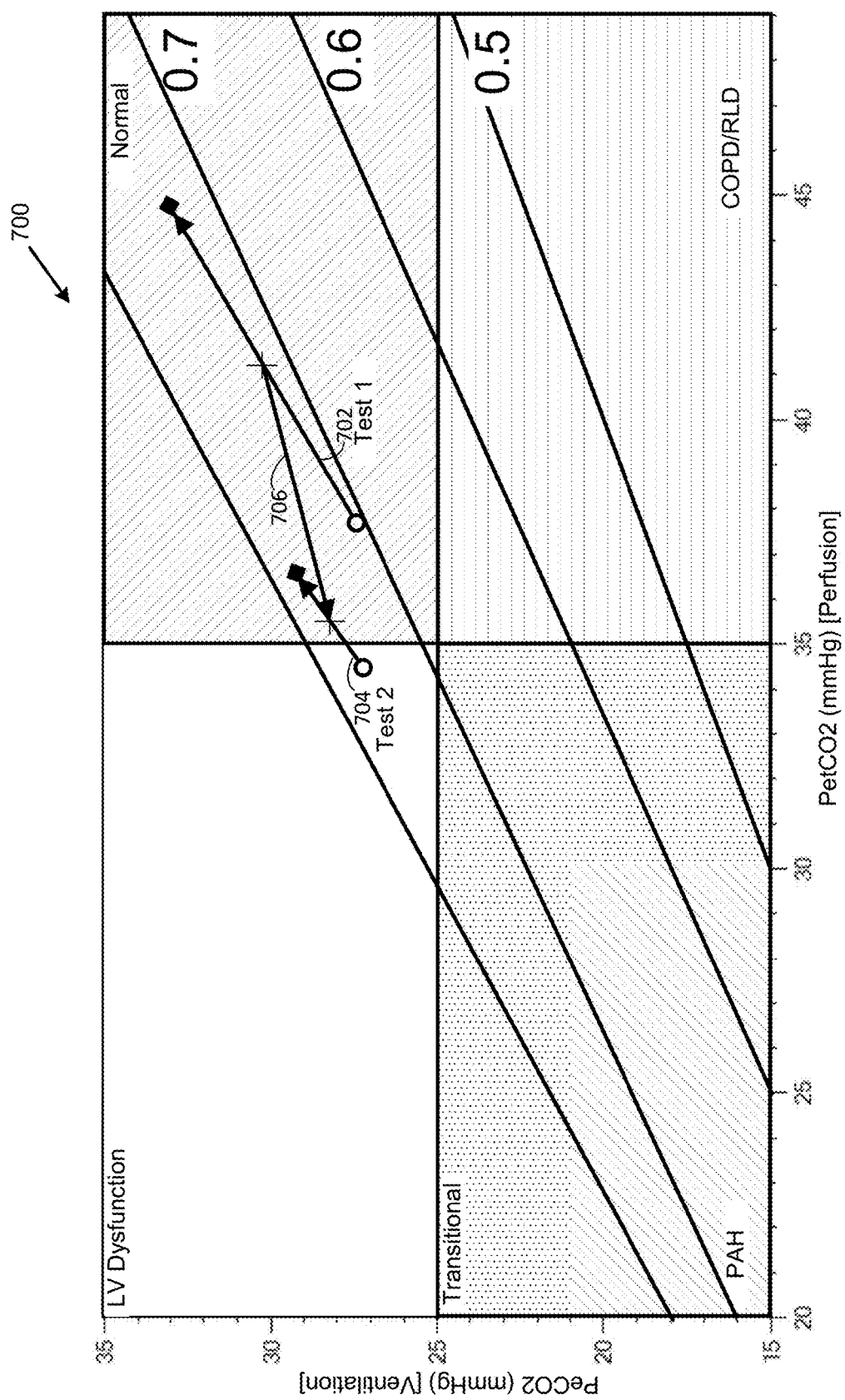
FIG. 7 illustrates the location of vectors for two CPX tests on the same patient.

In some implementations, the fixed format plot 600 illustrated in FIG. 6 is first populated with the CPX testing system measured variables mixed expired $CO_2$ ($PECO_2$) as the y value and end tidal $CO_2$ ($PetCO_2$) on the x axis, which are both plotted in mmHG in this example. These measurements may be used to define a vector for a test, as shown in FIG. 7. A vector 702 for Test 1 is shown, with one end at the resting value, indicated by an open circle, and one end on the end exercise value, indicated by a square box. An arrow symbol may then be added next to the square box to further indicate direction and amount of change from rest to exercise. A midpoint may be identified somewhere between the first end and the second end. The midpoint may be the geometric mean (i.e., the median x,y value) of the first end and the second end. In other words, the midpoint may be the half-way point between the first end and the second end of the test vector. In some implementations, other methods of determining a midpoint along the vector are used. The midpoint may be computed as any point along the vector. In this example, the midpoint is the geometric mean and is computed and identified on the plot using a + symbol. In this manner, the interpreting physician can easily identify the most likely disease type by observing the zone (or quadrant) in which the median of the vector (+ symbol) is located.

Step 2—Trend Plots

For patients who have had more than one CPX test (e.g., tests on more than one day), one vector may be plotted for each test. Referring to FIG. 7, two such vectors are shown (one per unique test), each with its own median value, are shown on a plot 700. In addition to the vector 702, FIG. 7 also include a vector 704. The test sequence is displayed—from the first test to the second test. An additional vector 706 is drawn from the median of the first vector to the median point of the second vector. In the example of FIG. 7, the resultant vector 706 of the medians is pointing left and down. This shows the interpreting physician that this patient's suspected disease is worsening or is not responding well to therapy, because the direction of the vector of the medians is proceeding from the Normal quadrant towards the Transitional quadrant. For a positive therapy responding patient, this vector should proceed upward and to the right indicating improvement in both lung ventilation and perfusion.

Figure 8:
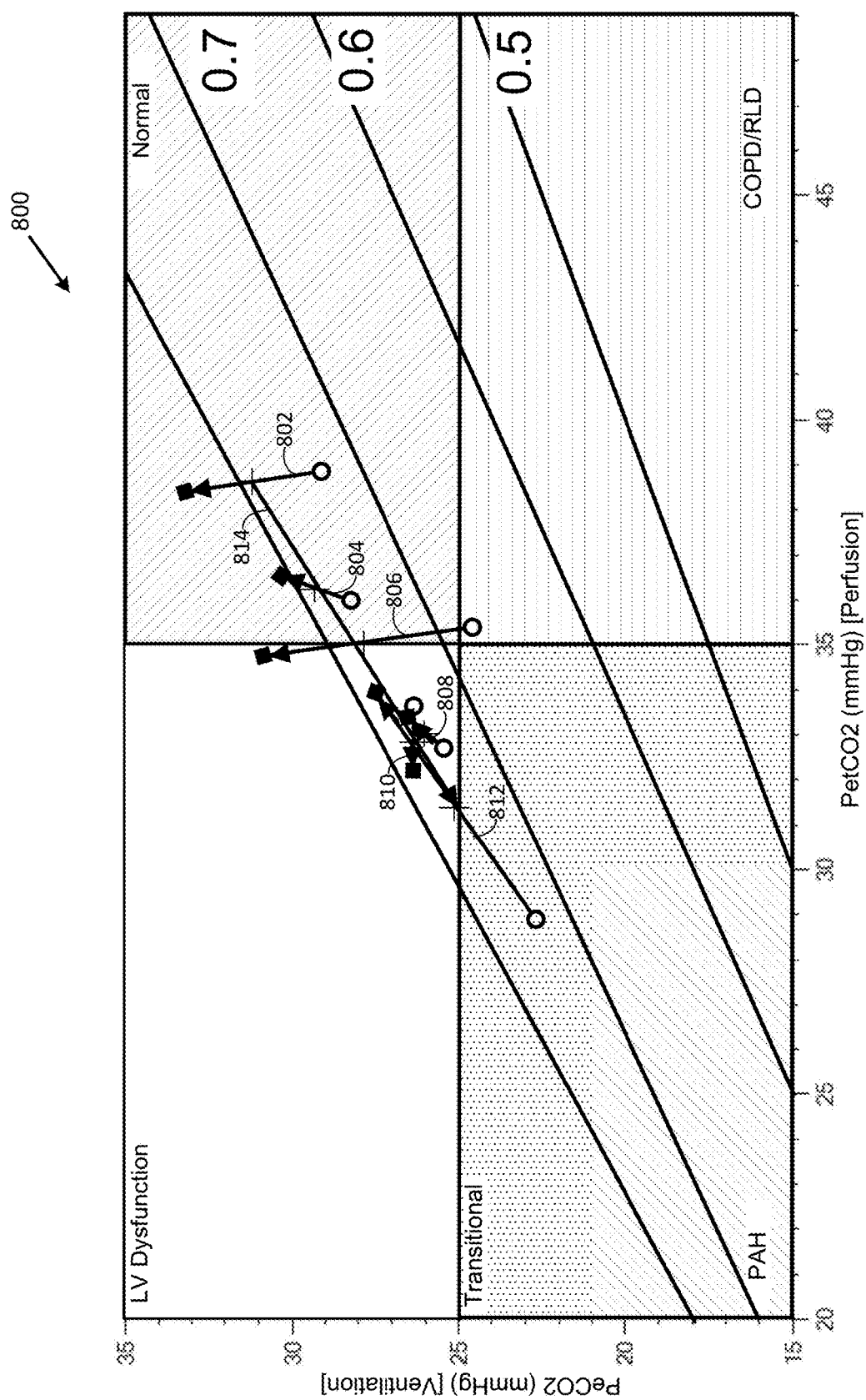
FIG. 8 illustrates the location of vectors for more than two CPX tests on the same patient.

Referring to FIG. 8, a plot 800 for a patient with multiple CPX tests (a total of 6 in this example, represented by vectors 802, 804, 806, 808, 810, and 812) can become very confusing. Additionally, in this example, a vector 814 is shown between the midpoint of the vector 802 (representing the earliest in time test for the patient) and the vector 812 (representing the latest in time test for the patient). Determining whether a patient is improving with therapy when more than two tests have been performed may be difficult. To preserve the intent of performing multiple tests, namely to determine if a patient is improving with therapy or not, in some implementations only the vectors associated with a subset of the patient's tests are presented. For example, a vector associated with an earlier in time (e.g., a first in time test performed by the patient) and a vector associated with a later in time (e.g., the last in time (or most recent) test performed by the patient) may be selected for display. In some implementations, the first vector may be selected based on the occurrence of an event such as the beginning of a treatment or a change in a treatment. Additionally, in some implementations, a vector of the means of these two tests corresponding to the selected vectors will be displayed similarly to FIG. 7.

The angle of the vector of the medians can also provide objective evidence of the effectiveness of a treatment. Referring to FIG. 7, the angle of a vector of the medians is determined by drawing a vertical (constant $PetCO_2$) line through the median of the first test. An angle can then be measured between the vertical line and the vector of the medians (i.e., the angle can be measured between the vector of the medians and a vertical vector pointing up).

If the angle is 0 to +90 degrees: Increased ventilation and perfusion post intervention shows the treatment had a positive effect.

If the angle is +90 to +180 degrees: Increased perfusion but decreased ventilation post intervention shows the treatment had mixed success.

If the angle is 0 to −90 degrees: Increased ventilation but decreased perfusion post intervention shows the treatment had mixed positive effect.

If the angle is −90 to −180 degrees: Decreased ventilation and decreased perfusion post intervention shows the treatment had no positive success.

This testing strategy will also work for fast acting therapies, such as a beta 2 agonist bronchodilator for either exercise induced asthma or for ameliorating hyperinflation during exercise in COPD patients. Because the CPX test is short (6 minutes), a first test is performed, after which the patient rests and a bronchodilator is given. Shortly thereafter, a second test is initiated. This would produce two vectors, the medians of which are used to generate a vector of the medians similarly to that described above. If this vector is pointing up and to the right (angle of the medians of the vectors >=0 and <=90), the bronchodilator provided an indication of reduced exercise induced bronchospasm with improved lung ventilation and perfusion.

Based on the determined physiological condition of a patient or the determined change in the condition of the patient based on the tests, one or more known treatment options for the condition or observed change in condition may be presented. A physician or caregiver may then select an appropriate option or determine an appropriate treatment or therapy change. An example therapy option for PAH could include the physician prescribing an endothelin receptor blocker (ERB) to reduce pulmonary vascular resistance and improve pulmonary blood flow or increase PETCO2 during rest and exercise.

Classification Scheme

Figure 5:
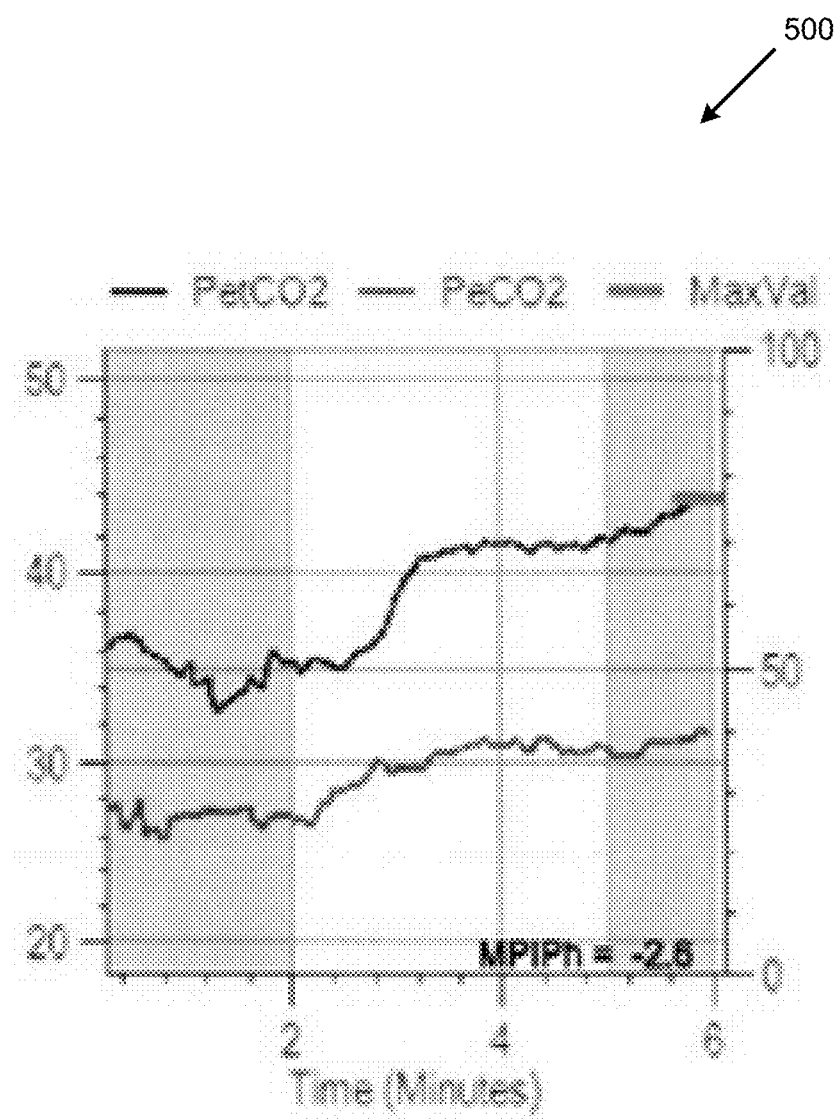
FIG. 5 illustrates a graph of a normal $PetCO_2$ and $PECO_2$ response to exercise over the course of the exercise test.

The primary description scheme is the design of the ventilation/perfusion plot as in FIG. 6 itself, which shows 4 quadrants for normal, COPD, and PAH. The lower left quadrant is further divided into a PAH zone and a Transition zone. These zones could be determined by visual observation of the graph 500 shown in FIG. 5. However, a further discussion is important to understand the meaning of each zone and the physiologic context of each:

Normal zone—Patients who fall into this zone based on the mean value of the vector described above have normal ventilation and perfusion changes with exercise. This zone is the target for any and all forms of therapy—a return to normal.

COPD—Patients who fall into this zone based on the mean value of the vector described above have slightly reduced perfusion but have clearly limited ventilation due to their lung disease, whether it be obstructive or restrictive.

LV dysfunction zone—The LV dysfunction zone reflects upon patients who demonstrate a reduction in pulmonary blood flow or cardiac output due to left ventricular pump dysfunction, whether it be systolic or diastolic. The reduced pulmonary blood flow is reflected by a blunting in the rise of PETCO2 during exercise. Regarding changes or increases in ventilation in patients with LV dysfunction, there is normally still an increase in $PECO_2$ or mixed expired $CO_2$ during exercise, unless the patient has co-morbid lung disease aside from their LV dysfunction.

PAH and Transitional—Patients whose median of the test vector falls into one of these zones have both defective perfusion and ventilation due to their pulmonary vascular restrictions. The zone identified as Transitional, however, means the patient may not be classified as a PAH patient, which has a poor prognosis, nor can the patient be classified as a COPD patient. Thus, they are in transition and progressing to increased disease severity. This transition zone shows evidence of reduced perfusion (lower $PETCO_2$ than normal or early LV dysfunction patient profile) and reduced ventilation ($PECO_2$), similar to the profile for patients with an early developing COPD profile. A patient test that produces a test vector median in the Transitional Zone is undergoing change, possible as a result of therapy. However, it could also be caused by the process of pulmonary vascular disease progression. This is where another CPX variable such as GxCap, a correlate of pulmonary capacitance, is helpful to show that the disease process progresses (reduced $PetCO_2$) until Pulmonary Vascular Resistance starts to increase, thereby placing a load on the Right Ventricle and further reducing blood flow and stroke volume ($O_2P$). The lungs can respond with bronchoconstriction (reduced $PECO_2$ and ventilation) or arteriolar vascular constriction to favor a more balanced V/Q ratio. As RV function deteriorates, capacitance, or GxCap, further decreases thus reducing cardiac output. Thus, the Transitional Zone is the early detection zone for suspected PAH. This may be shown, as in FIGS. 7 and 8, by the direction of the vector of the means (described above) proceeding downward and to the left.

To enhance the primary quadrant selection, such as with LV dysfunction, variables from other supportive diagnostic procedures (LV EF, mean PA and PCW pressure) may be displayed providing supportive evidence of worsening LV dysfunction. Worsening LV dysfunction can shift the vector of the medians into the transitional zone towards the PAH zone, indicating worsening RV disease progression. Other descriptive PAH metrics such as GxCap, a strong surrogate to pulmonary artery capacitance determined by hemodynamics, can be displayed in the V/Q plot or elsewhere to provide additional supportive evidence for a transition quadrant vector moving to the PAH zone. In some implementations, impressions statements may be generated based on GxCap or a GxCap recovery vector, which is discussed further below, if it is determined that the median or an endpoint of a patient's test vector falls into the PAH zone. Additionally, impressions statements may be generated based on the recovery vector when the test vector falls within the PAH zone. For example, an impressions statement may include text that indicates that the GxCap recovery vector (or the directional change during recovery of GxCap) is supportive evidence of PAH.

In some implementations, a recovery vector is determined and displayed. The recovery vector may be determined based on changes in various physiological measures that occur between the beginning and ending of a recovery phase of a test. In some implementations, the recovery vector is determined based on comparing a value determined during an exercise phase with a value determined during a recovery phase. The recovery vector may be based, for example, on GxCap. In some implementations, the recovery vector may be used for vaso-activity assessment.

Vaso-activity assessment may include pulmonary vascular function or relaxation testing and may be referred to as pulmonary vascular response to recovery testing. If the pulmonary vasculature responds favorably to an intervention, such as intravenous epoprostenol or adenosine or nitric oxide inhalation, a greater increase in the dynamic vector mid-point value (longer recovery segment of the vector shifted to the right) during the recovery period or a greater delta from end exercise to end recovery descriptive of drug induced vaso-relaxation may be observed. In some implementations, $PeCO_2$ changes are plotted on the y-axis against $PetCO_2$ changes on the x-axis. An improvement in $PetCO_2$ with use of a vaso-dilator drug during a test will extend the recovery segment and shift the vector downward, as seen in patients with normal pulmonary-vascular function.

Some implementations use the recovery vector to support or infer the presence of COPD based at least in part on detecting little change from end exercise to end recovery in the $PeCO_2/PetCO_2$ ratio due to a lower $PeCO_2$ value relative to $PetCO_2$.

Some implementations may include a plot of $PeCO_2$ and $PetCO_2$ with time. A drug that causes vaso relaxation such as those mentioned above as examples but not limited to such medications, may result in a test that shows an increase in the $PetCO_2$ immediately following drug administration, which may also be reflected in a more rightward end of recovery point in the V/Q plot.

Figure 12:
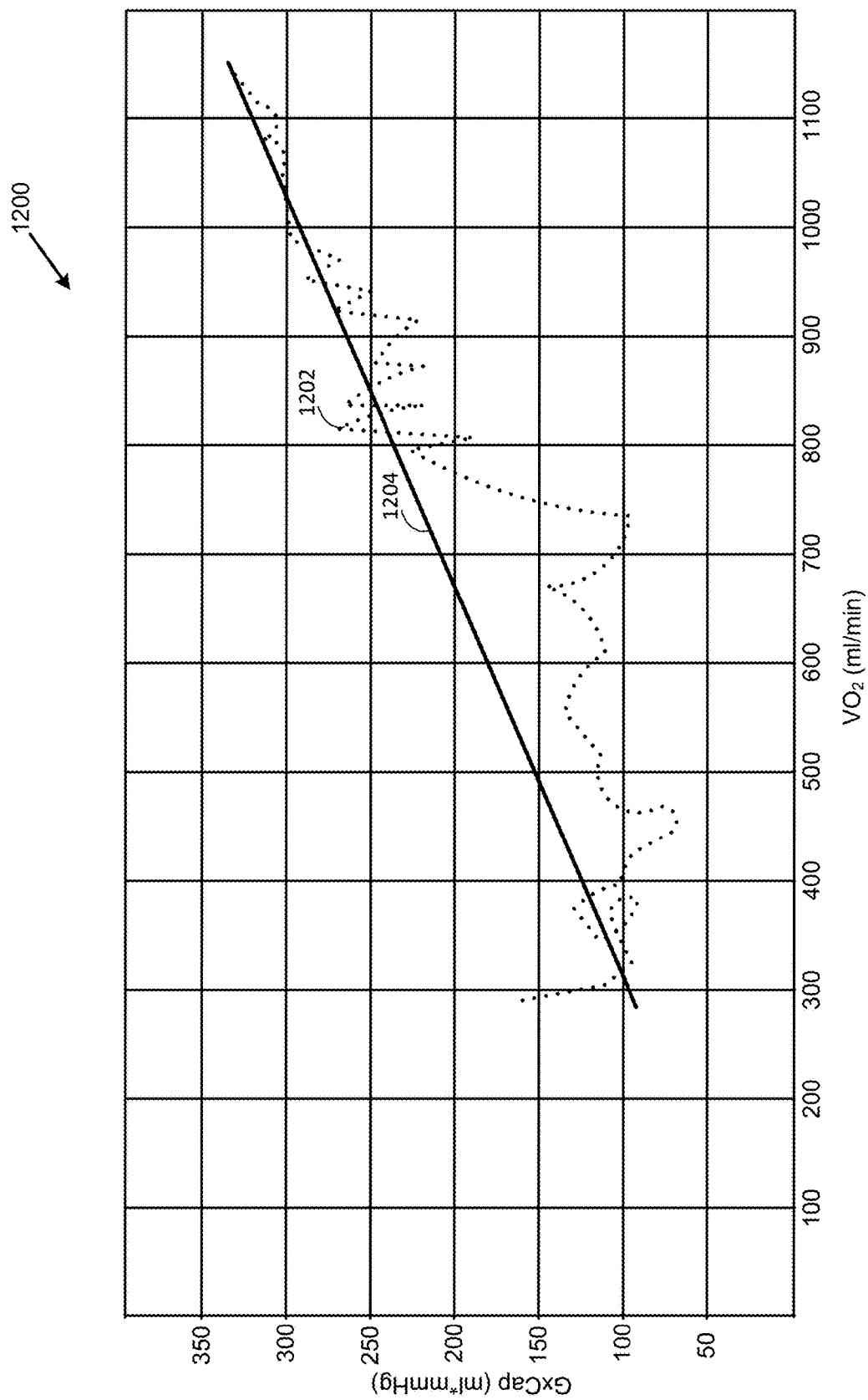
FIG. 12 illustrates an example plot of GxCap against $VO_2$ for a patient test.
Figure 13:
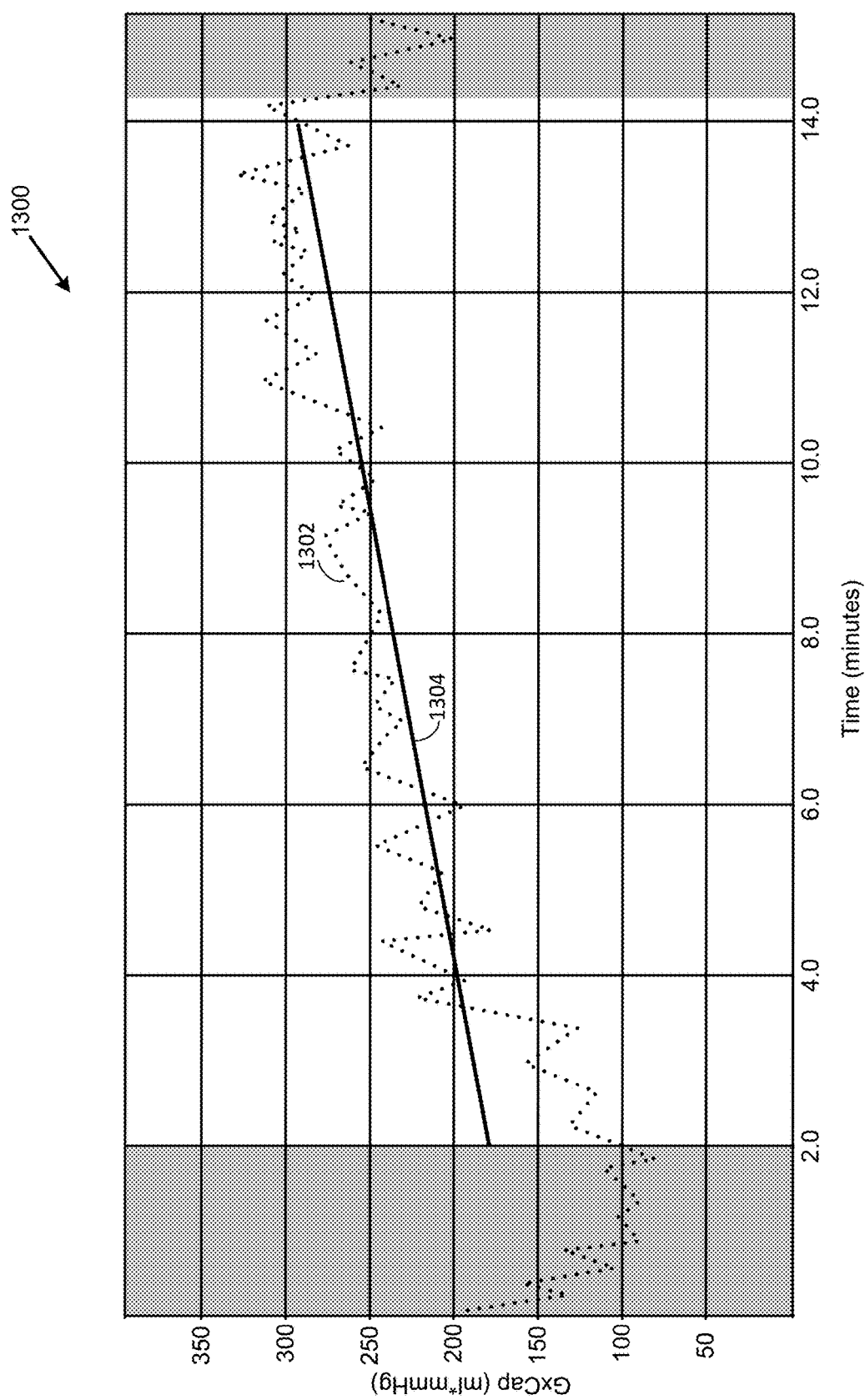
FIG. 13 illustrates an example plot of GxCap against time for a patient test.

GxCap may also be displayed on another plot. For example, GxCap may be plotted against time as shown in FIG. 12 or $VO_2$ as shown in FIG. 13. FIG. 12 shows a plot 1200 having a data series 1202 with GxCap values for the y-coordinate and $VO_2$ values for the x-coordinate. The values in the data series 1202 may be collected during a test. A regression line 1204 is also shown on the plot 1200. The regression line 1204 may be generated from some or all of the values in the data series 1202. A linear slope may be determined from the regression line 1204. FIG. 13 shows a plot 1300 having a data series 1302 with GxCap values for the y-coordinate and time values for the x-coordinate. The values in the data series 1302 may be collected during a test. For example, the data series 1302 may be from the same test used to generate the data series 1202. A regression line 1304 is also shown on the plot 1300. The regression line 1304 may be generated from some or all of the values in the data series 1302. A linear slope may be determined from the regression line 1304. Some implementations may use one or both of the slope of the regression line 1204 and the slope of the regression line 1304 for vaso-activity assessment or classifying a physiological condition of a patient. In some implementations, the plot 1200 or the plot 1300 may be generated for a CPX test based on determining that a midpoint or endpoint of the test vector is within the PAH zone of a plot (e.g., of the plot 600 shown in FIG. 6). For example, a user interface that shows the plot 1200 or the plot 1300 may automatically be displayed based on determining the test vector (or a portion of the test vector) is within the PAH or transitional zone.

Impressions Statement

Since most commercial providers of medical diagnostic equipment cannot "interpret" a test (a license to practice medicine is needed to interpret a test), the present method uses the term "Impressions" to verbalize the key findings of a CPX test. The physician, upon review of the test results, will either keep the computer-generated text as is, or he/she will edit the impressions statement. This is especially valuable to make sense out of complicated tests that fall into the Transition zone. This logic of this statement can also include other CPX variables collected during CPX testing. FIG. 9 shows example logic used to render an impressions statement in at least some implementations.

Figure 10A:
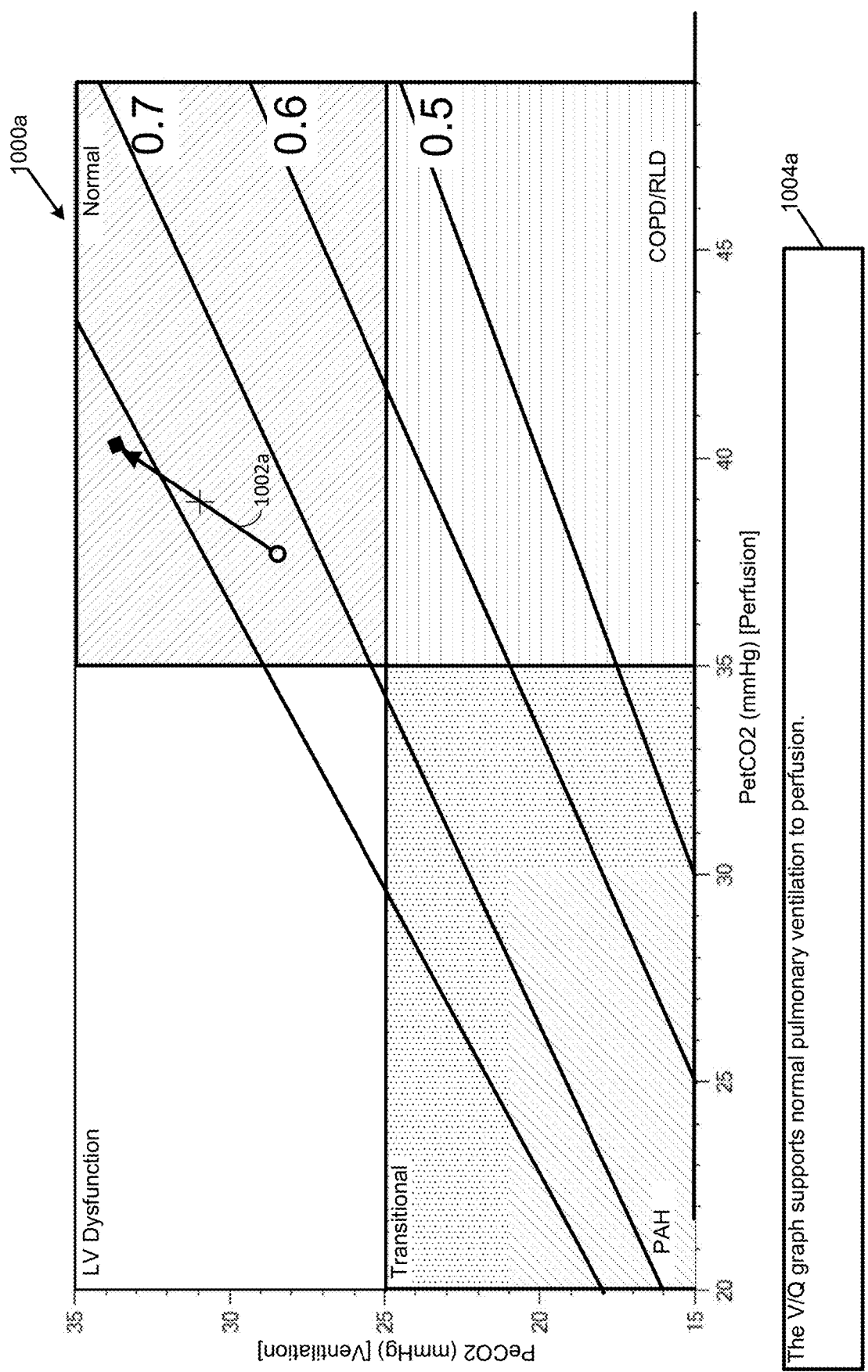
FIGS. 10a-d illustrates example populated tests for various physiological conditions or disease states.
Figure 10B:
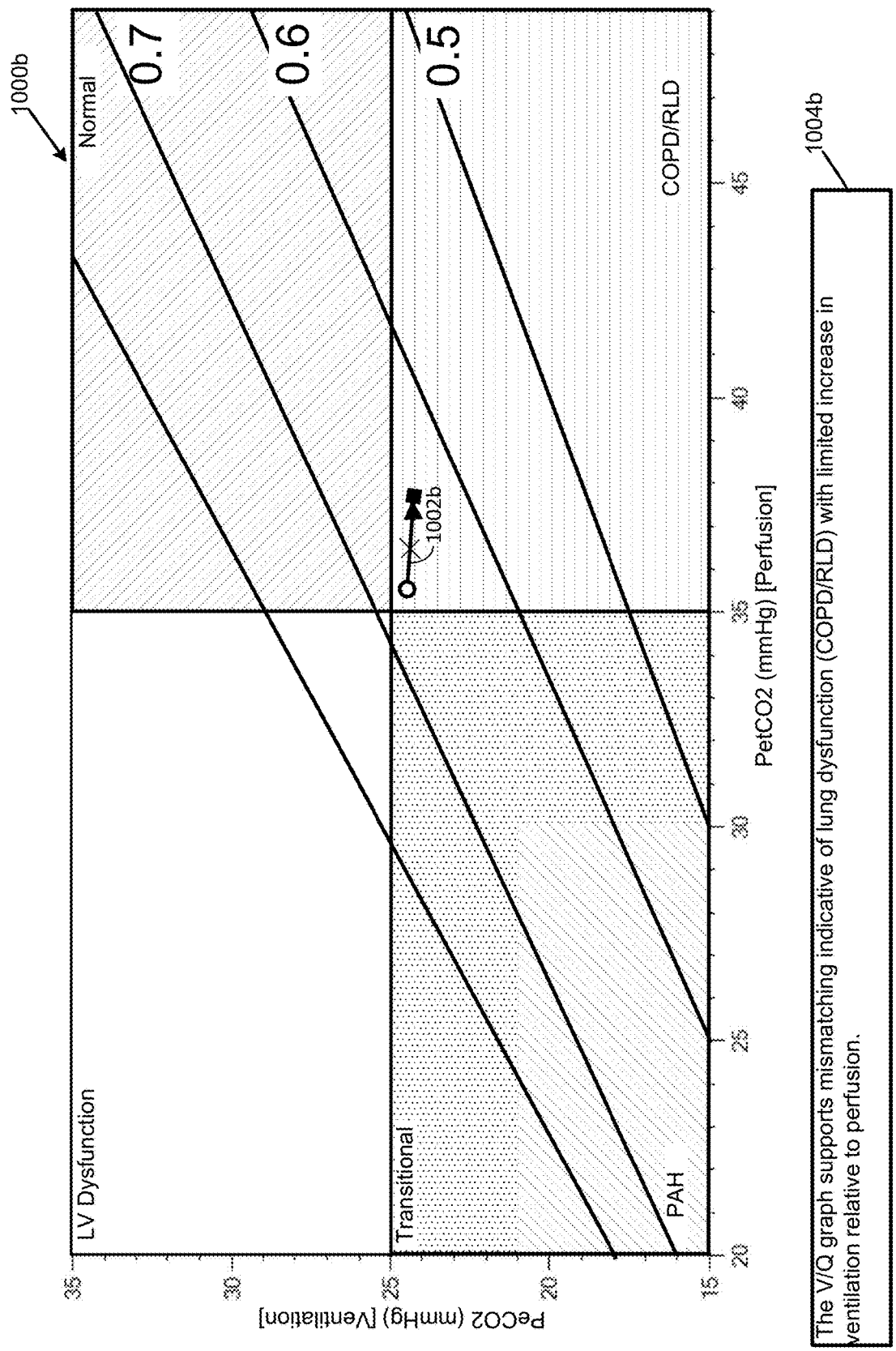
Figure 10C:
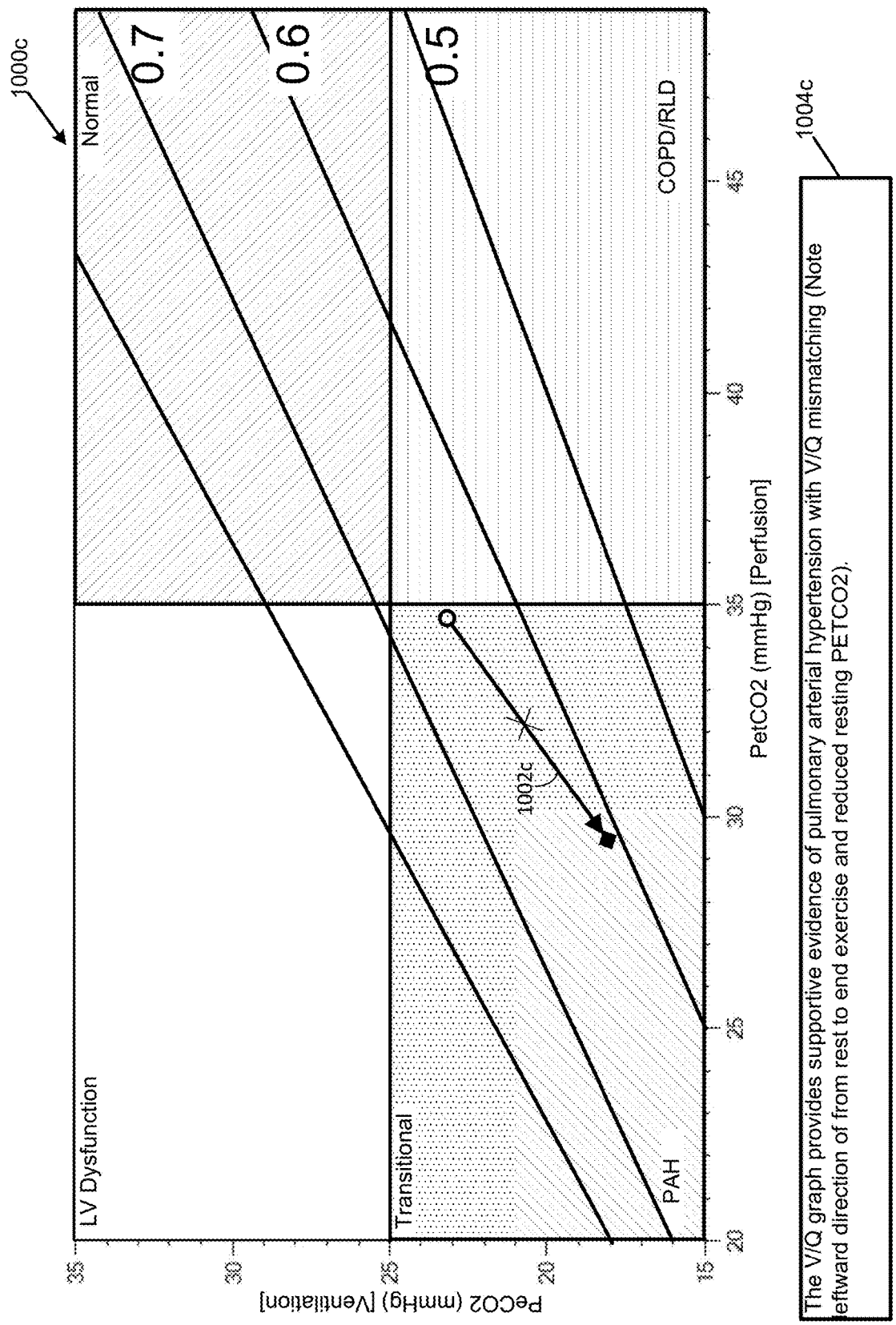
Figure 10D:
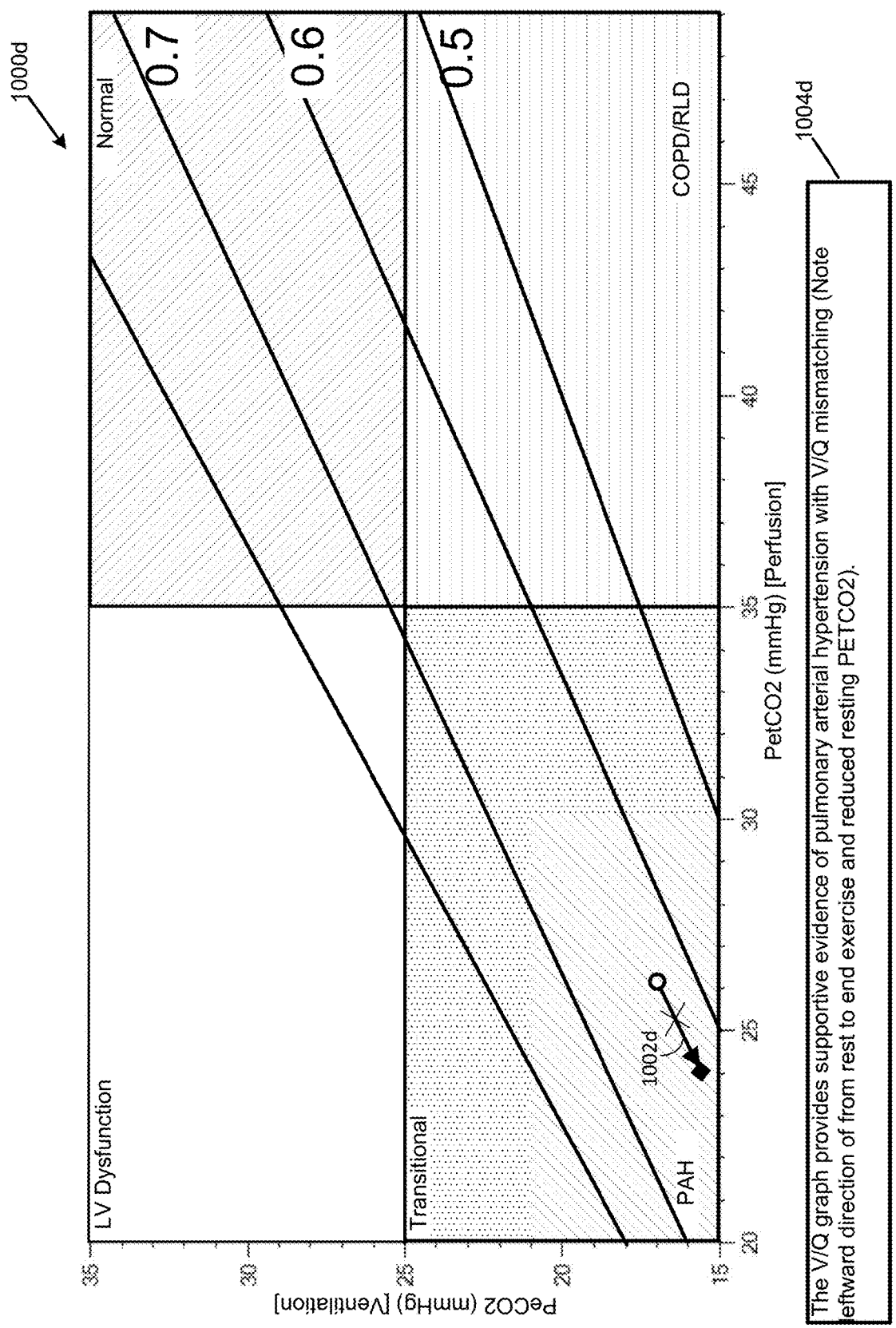

FIGS. 10a-d are provided to illustrate how example test reports would appear for four physiological conditions or disease states. FIG. 10a shows an example test report with a vector 1002a from a test with results in the normal zone. FIG. 10a also shows example impressions 1004a generated based on the test. FIG. 10b shows an example test report from a test with results in the COPD zone and example impressions 1004b generated based on the test. FIG. 10c shows an example test report with a vector 1002c from a test with results primarily in the transitional zone and example impressions 1004c generated based on the test. FIG. 10d shows an example test report with a vector 1002d from a test with results in the PAH zone and example impressions 1004d generated based on the test.

Figure 11:
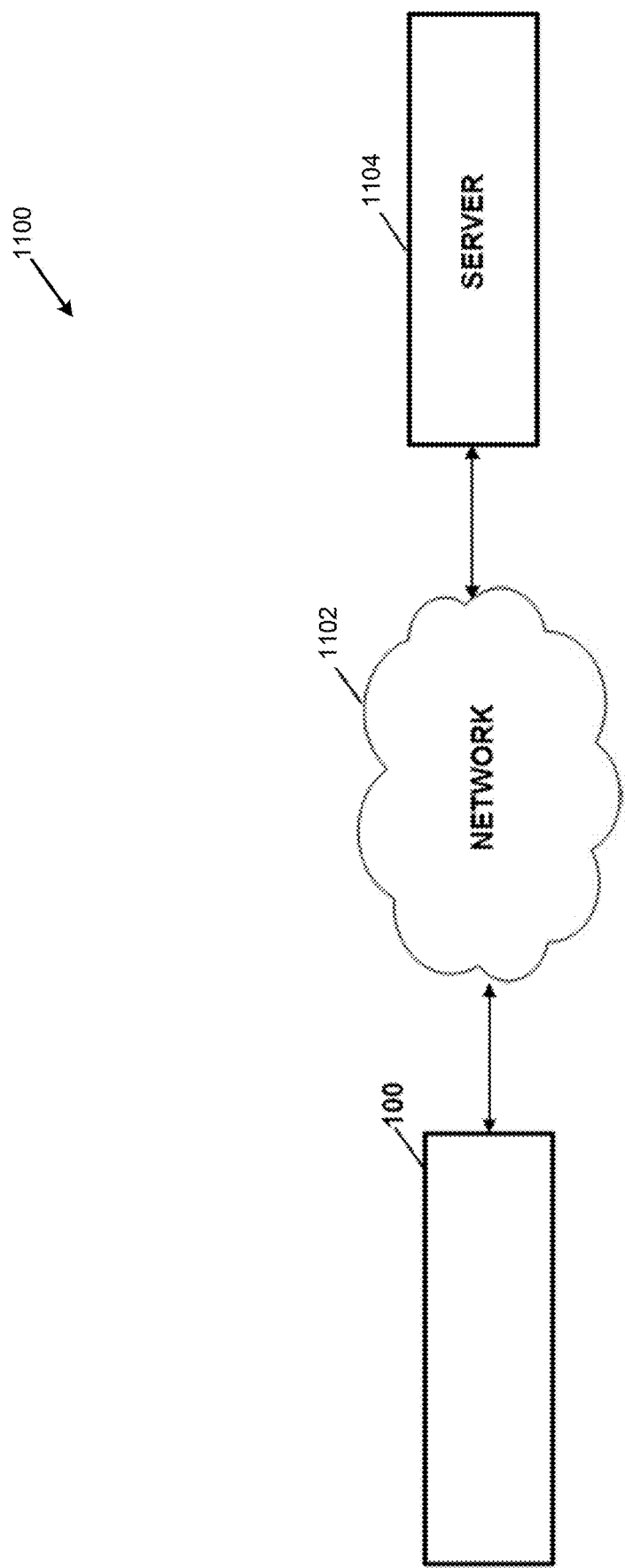
FIG. 11 illustrates an example networked CPX testing system.

Referring now to FIG. 11, an exemplary networked CPX testing system 1100 is illustrated. The networked CPX testing system 1100 can be used for remote testing and monitoring of patients. For example, the networked CPX testing system 1100 can be used in non-clinical environments, such as at the patient's home. In this example, the networked CPX testing system 1100 includes the CPX testing system 100, network 1102, and server 1104.

In some embodiments, the CPX testing system 100 is configured to send data associated with gas exchange tests (such as measurements of physiological parameters, index scores, etc.) to the server 1104 over the network 1102.

The network 1102 is an electronic communication network that facilitates communication between the CPX testing system 100 and the server 1104. An electronic communication network is a set of computing devices and links between the computing devices. The computing devices in the network use the links to enable communication among the computing devices in the network. The network 1102 can include routers, switches, mobile access points, bridges, hubs, intrusion detection devices, storage devices, stand-alone server devices, blade server devices, sensors, desktop computers, firewall devices, laptop computers, handheld computers, mobile telephones, and other types of computing devices.

In various embodiments, the network 1102 includes various types of links. For example, the network 1102 can include wired and/or wireless links, including Bluetooth, ultra-wideband (UWB), 802.11, ZigBee, and other types of wireless links. Furthermore, in various embodiments, the network 1102 is implemented at various scales. For example, the network 1102 can be implemented as one or more local area networks (LANs), metropolitan area networks, subnets, wide area networks (such as the Internet), or can be implemented at another scale.

The server 1104 comprises one or more computing devices. Various embodiments of computing devices have been described above. Further, in some embodiments, the server 1104 comprises a single server or a bank of servers. In another example, the server 1104 can be a distributed network server, commonly referred to as a "cloud" server.

In some embodiments, the server 1104 operates to receive data such as test results and physiological measurements from the CPX testing system 100. The server 1104 can then process the data and store it in one or more of a database or electronic medical records system.

In some embodiments, the server 1104 generates user interfaces, such as with a user interface engine, and transmits those user interfaces for display remotely. For example, the server 1104 may generate a web page comprising a user interface containing test data transmitted from the CPX testing system 100. The web page may then be transmitted to a computing device (e.g., a smart phone, personal computer, or tablet) of the patient or a caregiver.

Additionally, in some embodiments, the CPX testing system 100 communicates with a cellular phone or other network-connected computing device to access the network 1102. For example, the CPX testing system 100 may transmit data to the server 1104 via communication with a cell phone using Bluetooth. Other embodiments are possible as well.

This embodiments disclosed herein may be used in a scoring system based on several CPX test variables that are used to determine the height of "disease silos" graphic representations of the likeliness that the cause of a patient's dyspnea is one or more of the represented the disease silos. For example, embodiments may be incorporated into a system for determining and displaying "disease silos" such as those described in U.S. Pat. No. 10,010,264, titled "Pattern recognition system for quantifying the likelihood of the contribution of multiple possible forms of chronic disease to patient reported dyspnea" and dated Jul. 3, 2018. This allows a non-expert physician to emulate the thought process of experienced physicians and physiologists to determine the primary and secondary causes of the patient's shortness of breath. The methods described herein may improve the likeliness scoring by expanding the individual silo scoring schemes to include the Ventilation/Perfusion measurements of the present method to the scoring algorithms disclosed in U.S. Pat. No. 10,010,264.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

In the following several examples are given.

Example 1

A computer-implemented method comprising: receiving first cardiopulmonary exercise test data for a patient; plotting a first vector based on the first cardiopulmonary exercise test data, the first vector including a first point based on a rest value from the first cardiopulmonary exercise test data and a second point based on an exercise value from the first cardiopulmonary exercise test data, a first coordinate value of the first point and a first coordinate value of the second point being based on mixed expired $CO_2$ ($PECO_2$) and a second coordinate value of the first point and a second coordinate value of the second point being based on end tidal $CO_2$ ($PetCO_2$); and triggering display of the plotted vector over a coordinate grid.

Example 2

The computer-implemented method of example 1, wherein the plotting a first vector includes plotting an arrow that begins at the first point and ends at the second point.

Example 3

The computer-implemented method of example 1, further comprising: receiving second cardiopulmonary exercise test data for the patient, the first cardiopulmonary exercise test data corresponding to a first cardiopulmonary exercise test performed by the patient and the second cardiopulmonary exercise test data corresponding to a second cardiopulmonary exercise test performed by the patient; and plotting a second vector based on the second cardiopulmonary exercise test data.

Example 4

The computer-implemented method of example 3, wherein the receiving first cardiopulmonary exercise test data for the patient includes selecting cardiopulmonary test data corresponding to an earlier in time cardiopulmonary exercise test performed by the patient and the receiving second cardiopulmonary exercise test data for the patient includes selecting cardiopulmonary test data corresponding to a later in time cardiopulmonary test performed by the patient.

Example 5

The computer-implemented method of example 3, further comprising classifying the effectiveness of a treatment based on the first vector and the second vector.

Example 6

The computer-implemented method of example 5, wherein the classifying the effectiveness of the treatment based on the first vector and the second vector includes comparing a midpoint of the first vector to a midpoint of the second vector.

Example 7

The computer-implemented method of example 6, wherein the midpoint of the first vector is the geometric mean of the first point and the second point.

Example 8

The computer-implemented method of example 3, further comprising plotting a third vector, the third vector including a first point based on a midpoint of the first vector and a second point based on a midpoint of the second vector.

Example 9

The computer-implemented method of example 8, further comprising: determining a slope of the third vector; and classifying the effectiveness of a treatment based on the slope.

Example 10

The computer-implemented method of example 9, further comprising generating impressions statements based on the classification of the effectiveness of the treatment.

Example 11

The computer-implemented method of example 10, wherein the impressions statements include a recommendation or supportive information regarding continuation or change of treatment.

Example 12

The computer-implemented method of example 1, wherein the coordinate grid includes a plurality of physiological condition zones.

Example 13

The computer-implemented method of example 12, wherein the plurality of physiological condition zones includes a normal zone, a chronic obstructive and restrictive lung disease zone (COPD), a left ventricular (LV) dysfunction zone, a pulmonary arterial hypertension (PAH) zone, and a transitional zone.

Example 14

The computer-implemented method of example 1, further comprising determining a physiological condition classification for the patient based on the plotted vector.

Example 15

The computer-implemented method of example 14, further comprising generating impressions statements based on the physiological condition classification.

Example 16

The computer-implemented method of example 1, further comprising: plotting a midpoint of the first vector; and triggering display of the plotted midpoint over a coordinate grid having a plurality of physiological condition zones.

Example 17

A non-transitory computer-readable storage medium comprising instructions stored thereon that, when executed by at least one processor, are configured to cause a computing system to: receive first cardiopulmonary exercise test data for a patient; plot a first vector based on the first cardiopulmonary exercise test data, the first vector including a first point based on a rest value from the first cardiopulmonary exercise test data and a second point based on an exercise value from the first cardiopulmonary exercise test data, a first coordinate value of the first point and a first coordinate value of the second point being based on mixed expired $CO_2$ ($PECO_2$) and a second coordinate value of the first point and a second coordinate value of the second point being based on end tidal $CO_2$ ($PetCO_2$); and trigger display of the plotted vector over a coordinate grid having a plurality of physiological condition zones.

Example 18

The non-transitory computer-readable storage medium of example 17, wherein the instructions further cause the computing system to classify the patient with respect to a physiologic condition based on the first vector and the physiological condition zones.

Example 19

A non-transitory computer-readable storage medium comprising instructions stored thereon that, when executed by at least one processor, are configured to cause a computing system to: receive cardiopulmonary exercise test data for a patient; and plot a recovery vector based on the first cardiopulmonary exercise test data.

Example 20

The non-transitory computer-readable storage medium of example 19, wherein the recovery vector includes a first recovery vector point based on an end exercise value from the cardiopulmonary exercise test data and a second recovery vector point based on an end recovery value from the cardiopulmonary exercise test data.

Example 21

The non-transitory computer-readable storage medium of example 18, wherein a first coordinate value of the first recovery vector point and a first coordinate value of the second recovery vector point are based on GxCap.

Example 22

The non-transitory computer-readable storage medium of example 18, wherein a first recovery vector point is determined at the end of an exercise phase and a second recovery vector point is determined at the end of a recovery phase.

Example 23

The non-transitory computer-readable storage medium of example 19, wherein the recovery vector is based on a directional change in GxCap versus time.

Example 24

A system comprising: a flow sensor configured to sense a respiratory flow of a patient; an analyzer configured to determine a composition of at least a portion of the respiratory flow of the patient; and a computing device configured to: receive first cardiopulmonary exercise test data for a patient; plot a first vector based on the first cardiopulmonary exercise test data, the first vector including a first point based on a rest value from the first cardiopulmonary exercise test data and a second point based on an exercise value from the first cardiopulmonary exercise test data, a first coordinate

Example 25

The system of example 24, wherein the analyzer includes a carbon dioxide ($CO_2$) sensor.

Example 26

The system of example 25, wherein the analyzer includes an oxygen ($O_2$) sensor.

Example 27

The system of example 25, wherein the analyzer does not include an oxygen ($O_2$) sensor.

Example 28

The system of example 24, wherein the analyzer is an oxygen-sensorless analyzer.

What is claimed is:

1. A computer-implemented method comprising:
   receiving first cardiopulmonary exercise test data for a patient, the first cardiopulmonary exercise test data corresponding to a first submaximal cardiopulmonary exercise test performed by the patient;
   plotting a first vector based on the first cardiopulmonary exercise test data, the first vector including a first point based on a rest value from the first cardiopulmonary exercise test data and a second point based on an exercise value from the first cardiopulmonary exercise test data, a first coordinate value of the first point and a first coordinate value of the second point being based on mixed expired CO2 (PECO2) and a second coordinate value of the first point and a second coordinate value of the second point being based on end tidal CO2 (PetCO2);
   triggering display of the plotted first vector over a coordinate grid having a plurality of isopleths and a plurality of physiological condition zones, wherein the plurality of physiological condition zones are different than the plurality of isopleths;
   receiving second cardiopulmonary exercise test data for the patient, the second cardiopulmonary exercise test data corresponding to a second submaximal cardiopulmonary exercise test performed by the patient;
   plotting a second vector based on the second cardiopulmonary exercise test data; and
   classifying the effectiveness of a treatment based on comparing a midpoint of the first vector to a midpoint of the second vector.

2. The computer-implemented method of claim 1, wherein the receiving first cardiopulmonary exercise test data for the patient includes selecting cardiopulmonary test data corresponding to an earlier in time cardiopulmonary exercise test performed by the patient and the receiving second cardiopulmonary exercise test data for the patient includes selecting cardiopulmonary test data corresponding to a later in time cardiopulmonary test performed by the patient.

3. The computer-implemented method of claim 1, further comprising plotting a third vector, the third vector including a first point based on a midpoint of the first vector and a second point based on a midpoint of the second vector.

4. The computer-implemented method of claim 3, further comprising:
   determining a slope of the third vector; and
   classifying the effectiveness of a treatment based on the slope.

5. The computer-implemented method of claim 4, further comprising generating impressions statements that include supportive information regarding continuation or change of treatment based on the classification of the effectiveness of the treatment.

6. The computer-implemented method of claim 4, further comprising:
   determining a physiological condition classification for the patient based on the plotted vector; and
   generating impressions statements based on the physiological condition classification.

7. The computer-implemented method of claim 4, further comprising:
   plotting a midpoint of the first vector.

8. A non-transitory computer-readable storage medium comprising instructions stored thereon that, when executed by at least one processor, are configured to cause a computing system to:
   receive first cardiopulmonary exercise test data for a patient, the first cardiopulmonary exercise test data corresponding to a first submaximal cardiopulmonary exercise test performed by the patient;
   plot a first vector based on the first cardiopulmonary exercise test data, the first vector including a first point based on a rest value from the first cardiopulmonary exercise test data and a second point based on an exercise value from the first cardiopulmonary exercise test data, a first coordinate value of the first point and a first coordinate value of the second point being based on mixed expired CO2 (PECO2) and a second coordinate value of the first point and a second coordinate value of the second point being based on end tidal CO2 (PetCO2);
   trigger display of the plotted first vector over a coordinate grid having a plurality of isopleths and a plurality of physiological condition zones, wherein the plurality of physiological condition zones are different than the plurality of isopleths;
   receive second cardiopulmonary exercise test data for the patient, the second cardiopulmonary exercise test data corresponding to a second submaximal cardiopulmonary exercise test performed by the patient;
   plot a second vector based on the second cardiopulmonary exercise test data; and
   classify the effectiveness of a treatment based on comparing a midpoint of the first vector to a midpoint of the second vector.

9. The non-transitory computer-readable storage medium of claim 8, wherein the instructions further cause the computing system to:
   plot a recovery vector based on the first cardiopulmonary exercise test data, the recovery vector including a first recovery vector point based on an exercise value from the first cardiopulmonary exercise test data and a second recovery vector point based on a recovery value from the first cardiopulmonary exercise test data.

10. The non-transitory computer-readable storage medium of claim 9, wherein a first coordinate value of the first recovery vector point and a first coordinate value of the second recovery vector point are based on GxCap.

11. The non-transitory computer-readable storage medium of claim 9, wherein the first recovery vector point is determined at the end of an exercise phase and the second recovery vector point is determined at the end of a recovery phase.

12. The non-transitory computer-readable storage medium of claim 8, wherein the instructions further cause the computing system to classify the patient with respect to a physiologic condition based on the first vector.

13. A system comprising: a flow sensor configured to sense a respiratory flow of a patient; an analyzer configured to determine a composition of at least a portion of the respiratory flow of the patient; and a computing device configured to:
    receive first cardiopulmonary exercise test data for a patient, the first cardiopulmonary exercise test data corresponding to a first submaximal cardiopulmonary exercise test performed by the patient;
    plot a first vector based on the first cardiopulmonary exercise test data, the first vector including a first point based on a rest value from the first cardiopulmonary exercise test data and a second point based on an exercise value from the first cardiopulmonary exercise test data, a first coordinate value of the first point and a first coordinate value of the second point being based on mixed expired CO2 (PECO2) and a second coordinate value of the first point and a second coordinate value of the second point being based on end tidal CO2 (PetCO2);
    trigger display of the plotted first vector over a coordinate grid having a plurality of isopleths and a plurality of physiological condition zones, wherein the plurality of physiological condition zones are different than the plurality of isopleths;
    receive second cardiopulmonary exercise test data for the patient, the second cardiopulmonary exercise test data corresponding to a second submaximal cardiopulmonary exercise test performed by the patient;
    plot a second vector based on the second cardiopulmonary exercise test data; and
    classify the effectiveness of a treatment based on comparing a midpoint of the first vector to a midpoint of the second vector.

14. The system of claim 13, wherein the analyzer includes a carbon dioxide ($CO_2$) sensor.

15. The system of claim 14, wherein the analyzer does not include an oxygen ($O_2$) sensor.

16. The system of claim 13, wherein the computing device is further configured to:
    plot a third vector, the third vector including a first point based on a midpoint of the first vector and a second point based on a midpoint of the second vector;
    determine a slope of the third vector; and
    classify the effectiveness of a treatment based on the slope.

17. The system of claim 13, wherein the plurality of physiological condition zones includes a normal zone, a chronic obstructive and restrictive lung disease zone (COPD), a left ventricular (LV) dysfunction zone, a pulmonary arterial hypertension (PAH) zone, and a transitional zone.

* * * * *